(12) United States Patent
Wada et al.

(10) Patent No.: US 7,132,455 B2
(45) Date of Patent: Nov. 7, 2006

(54) PHTHALAMIDE DERIVATIVES

(75) Inventors: Katsuaki Wada, Tochigi (JP); Takuya Gomibuchi, Ibaraki (JP); Yasushi Yoneta, Kazo (JP); Yuichi Otsu, Tochigi (JP); Katsuhiko Shibuya, Tochigi (JP); Hanako Okuya, Ibaraki (JP); Rüdiger Fischer, Pulheim (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 10/517,859

(22) PCT Filed: Jun. 11, 2003

(86) PCT No.: PCT/EP03/06105

§ 371 (c)(1),
(2), (4) Date: Aug. 16, 2005

(87) PCT Pub. No.: WO04/000796

PCT Pub. Date: Dec. 31, 2003

(65) Prior Publication Data

US 2006/0035967 A1 Feb. 16, 2006

(30) Foreign Application Priority Data

Jun. 20, 2002 (JP) .............................. 2002-180028

(51) Int. Cl.
*A01N 37/24* (2006.01)
*C07C 233/64* (2006.01)
(52) U.S. Cl. .............. 514/616; 514/616; 514/618; 514/620; 564/123; 564/162; 564/164; 564/176; 564/179
(58) Field of Classification Search ............... 514/616, 514/618, 620; 564/123, 162, 164, 176, 179
See application file for complete search history.

(56) References Cited

U.S. PATENT DOCUMENTS

| | | | |
|---|---|---|---|
| 5,922,732 A | 7/1999 | Urch et al. ................ | 514/304 |
| 5,968,947 A | 10/1999 | Urch et al. ................ | 514/299 |
| 6,093,726 A | 7/2000 | Urch et al. ................ | 514/299 |
| 6,174,894 B1 | 1/2001 | Urch et al. ................ | 514/299 |
| 6,177,442 B1 | 1/2001 | Urch et al. ................ | 514/299 |
| 6,207,676 B1 | 3/2001 | Urch et al. ................ | 514/304 |
| 6,291,474 B1 | 9/2001 | Brightwell et al. ......... | 514/299 |
| 6,362,369 B1 | 3/2002 | Tohnishi et al. ............ | 564/156 |
| 6,391,883 B1 | 5/2002 | Urch et al. ................ | 514/255 |
| 6,559,341 B1 | 5/2003 | Tohnishi et al. ............ | 564/442 |
| 6,573,275 B1 | 6/2003 | Urch et al. ................ | 514/304 |
| 6,603,044 B1 | 8/2003 | Tohnishi et al. ............ | 564/154 |
| 6,639,109 B1 | 10/2003 | Sanpei et al. ............... | 564/501 |
| 6,642,379 B1 | 11/2003 | Furuya et al. .............. | 544/88 |
| 6,747,041 B1 | 6/2004 | Katsuhira et al. .......... | 514/307 |
| 6,864,289 B1 | 3/2005 | Tohnishi et al. ............ | 514/617 |
| 2001/0041814 A1 | 11/2001 | Tohnishi et al. ............ | 564/156 |
| 2002/0061913 A1 | 5/2002 | Urch et al. ................ | 514/366 |
| 2003/0055287 A1 | 3/2003 | Tohnishi et al. ............ | 564/154 |

OTHER PUBLICATIONS

Tetrahedron Letters, vol. 29, No. 44, (month unavailable) 1988, pp. 5595-5598 James L. Charlton et al, "Substituent Effects on the Photochemistry of o-Tolualdehydes".
J. Org. Chem., 29, Jan. 13, 1964, pp. 1-11, William A. Sheppard "α-Fluorinated Ethers. I. Aryl Fluoroalkyl Ethers".
Angew Chem. Int. Ed. Engl. 24, (month unavailable) 1985, pp. 871-872, Xing-ya Li et al, "Reactions of Per(chloro,fluoro)ethanes with Aryloxide and Alkoxide Ions-Evidence for Chlorophilic Attack on C-Cl Bonds".
J. Med. Chem., 10, (month unavailable) 1967, pp. 982-983, Edith G. Dfaz$_{DE}$ Toranzo et al "Syntheses of Unsymmetric o-Phthalic Acid Diamides".
J. Org. Chem., 46, (month unavailable) 1981, pp. 175-177, John W. Verbicky, Jr. et al, "Thermolysis of N-Alkyl-Substituted Phthalamic Acids. Steric Inhibition of Imide Formation".

*Primary Examiner*—Kamal A. Saeed
*Assistant Examiner*—Yong Chu
(74) *Attorney, Agent, or Firm*—Richard E. L. Henderson

(57) ABSTRACT

This invention relates to novel phthalamide derivatives of formula (I)

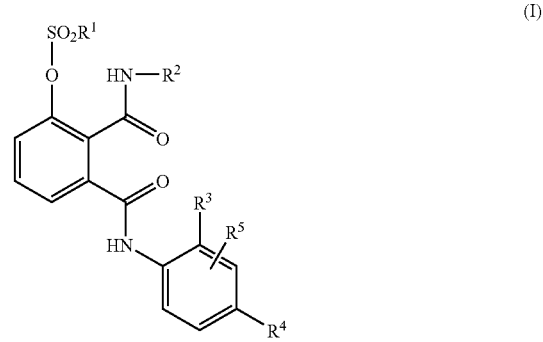

wherein $R^1$, $R^2$, $R^3$, $R^4$, and $R^5$ have the meanings given in the disclosure, to processes for their preparation, and to their use as insecticidal agents in agricultural and horticultural field.

8 Claims, No Drawings

PHTHALAMIDE DERIVATIVES

The present patent application has been filed under 35 U.S.C. 371 as a national stage application of PCT/EP2003/006105, filed Jun. 11, 2003, which was published in English as International Patent Publication WO 2004/000796 on Dec. 31, 2003, which is entitled to the right of priority of Japanese Patent Application 2002-180028, filed Jun. 20, 2002.

It is already known that certain phthalamide derivatives show an action as insecticide (cf.: EP 0 919 542-A2, EP 1 006 107-A2, WO 01/00575, WO 01/00599, WO 01/21576).

Further, it is already known that certain phthalamide derivatives show an action as pharmaceutical (cf.: EP 0 119 428-A2).

There have now been found novel phthalamide derivatives of the formula (I)

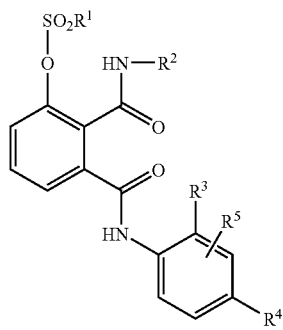

(I)

wherein
$R^1$ represents alkyl which may be optionally halogen-substituted,
$R^2$ represents alkyl which may be optionally substituted or cycloalkyl which may be optionally substituted,
$R^3$ represents hydrogen atom, halogen, or alkyl which may be optionally halogen-substituted,
$R^4$ represents hydrogen atom, halogen-substituted alkyl, halogen-substituted alkoxy, halogen-substituted phenyl, or halogen-substituted phenoxy, and
$R^5$ represents hydrogen atom, halogen, or alkyl which may be optionally halogen-substituted.

Depending on the nature and the number of substituents, the compounds of the formula (I) may be present as geometrical and/or optical isomers, regioisomers or configurational isomers or isomer mixtures thereof of varying composition. What is claimed by the invention are both the pure isomers and the isomer mixtures.

The compounds of the formula (I), according to the invention, can be obtained by a process in which
a) compounds of the formula (II)

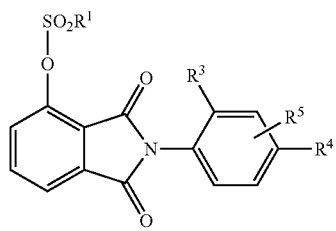

(II)

wherein $R^1$, $R^3$, $R^4$ and $R^5$ have the same definitions as aforementioned, are reacted with compounds of the formula (III)

$$H_2N-R^2 \quad (III)$$

wherein $R^2$ has the same definition as aforementioned, in the presence of inert solvents, and if appropriate, in the presence of a base, or b) compounds of the formula (IV)

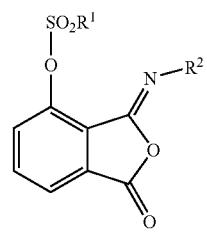

(IV)

wherein $R^1$ and $R^2$ have the same definitions as aforementioned, are reacted with compounds of the formula (V)

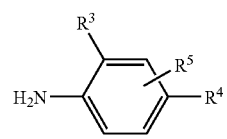

(V)

wherein $R^3$, $R^4$ and $R^5$ have the same definitions as aforementioned, in the presence of inert solvents, and if appropriate, in the presence of an acid catalyst, or c) compounds of the formula (VI)

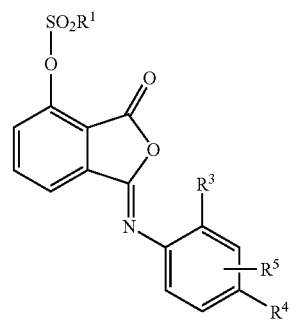

(VI)

wherein $R^1$, $R^3$, $R^4$ and $R^5$ have the same definitions as aforementioned, are reacted with compounds of the formula (III),

$$H_2N-R^2 \quad (III)$$

wherein $R^2$ has the same definition as aforementioned, in the presence of inert solvents, and if appropriate, in the presence of a acid catalyst, or d) in case of preparing the compounds of the formula (I) in which $R^2$ represents alkylsulfinylalkyl or alkylsulfonylalkyl: compounds of the formula (Id)

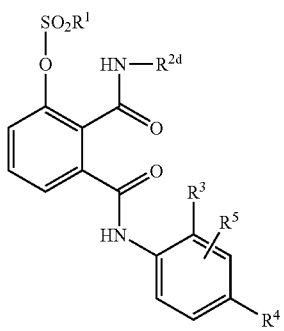

wherein $R^{2d}$ represents alkylthioalkyl, $R^1$, $R^3$, $R^4$ and $R^5$ have the same definitions as aforementioned, are reacted with an oxidizing agent, in the presence of inert solvents.

The phthalamide derivatives of the formula (I) provided by the present invention show a strong insecticidal action.

According to the present invention the phthalamide derivatives of the formula (I) are included conceptually in the compounds represented by the general formula described in EP 0 919 542-A2 or EP 1 006 107-A2. In said publications, however, the phthalamide derivatives of the formula (I) of the present invention are not specifically disclosed.

The compounds of the formula (I) of the present invention surprisingly show very strong insecticidal action, compared with the compounds specifically described in the above-mentioned patent publications, which are similar to the formula (I) of the present invention and particularly exhibit excellent insecticidal action against lepidopteran harmful insects. Moreover, the compounds of the formula (I) of the present invention show systemic insecticidal action.

In the present specification, "halogen" and halogen part in "alkyl which may be halogen-substituted", "halogen-substituted alkyl", "halogen-substituted alkoxy", "halogen-substituted phenyl" and "halogen-substituted phenoxy" represents fluoro, chloro, bromo or iodo, and is preferably fluoro, chloro or bromo.

"Alkyl" and alkyl part in each group "alkoxy", "alkylthio", "alkylsulfinyl" and "alkylsulfonyl" can be a straight-chain or branched-chain and there can be mentioned, for example, methyl, ethyl, n- or iso-propyl, n-, iso-, sec- or tert-butyl, n-, iso-, neo-, tert-pentyl, 2-methylbutyl, n-, iso- or sec-hexyl, etc.

"Cycloalkyl" includes, for example, cyclopropyl, cyclobutyl, cyclopentyl, cyclohexyl, cycloheptyl, cyclooctyl, etc.

"Halogen-substituted alkyl" represents a straight-chain or branched-chain alkyl, at least one of which hydrogen is substituted with halogen, and there can be mentioned, for example, $C_{1-6}$ alkyl substituted with 1–9 fluoro and/or chloro, and as its specific examples there can be mentioned, difluoromethyl, trifluoromethyl, 2-fluoroethyl, 2-chloroethyl, 2,2,2-trifluoroethyl, 1,1,2,2-tetrafluoroethyl, 1,1,2,2,2-pentafluoroethyl, 2-chloro-1,1,2-trifluoroethyl, 3-fluoropropyl, 3-chloropropyl, 1-methyl-2,2,2-trifluoroethyl, 2,2,3,3,3-pentafluoropropyl, 1,2,2,3,3,3-hexafluoropropyl, perfluoroisopropyl, perfluorobutyl, 2,2,3,3,4,4,5,5,5-nonafluoropentyl, 3,3,4,4,5,5,6,6,6-nonafluorohexyl, etc.

Halogen-substituted alkyl part in "halogen-substituted alkoxy" can be of the same definition as the aforementioned "halogen-substituted alkyl" and as "halogen-substituted alkoxy" there can be mentioned specifically, for example, difluoromethoxy, trifluoromethoxy, 2-fluoroethoxy, 2-chloroethoxy, 2-bromoethoxy, 2,2,2-trifluoroethoxy, etc.

"Halogen-substituted phenyl" and halogen-substituted phenyl part in "halogen-substituted phenoxy" can represent phenyl substituted with 1-3, preferably 1-2 of the aforementioned "halogen" and as its specific examples there can be mentioned 2-, 3- or 4-fluorophenyl, 2-, 3- or 4-chlorophenyl, 2,3-, 2,4-, 2,5-, 2,6-, 3,4- or 3,5-dichlorophenyl, etc.

In the compounds of the aforementioned formula (I), preferably $R^1$ represents $C_{1-6}$ alkyl which may be optionally fluoro-substituted, chloro-substituted or bromo-substituted, $R^2$ represents $C_{1-6}$ alkyl which may be optionally fluoro-substituted, chloro-substituted, bromo-substituted, $C_{1-4}$ alkoxy-substituted, $C_{1-4}$ alkylthio-substituted, $C_{1-4}$ alkylsulfinyl-substituted, or $C_{1-4}$ alkylsulfonyl-substituted, or represents $C_{3-6}$ cycloalkyl which may be optionally halogen-substituted or $C_{1-4}$ alkyl-substituted, $R^3$ represents hydrogen atom or halogen, or represents $C_{1-6}$ alkyl which may be optionally fluoro-substituted, chloro-substituted or bromo-substituted, $R^4$ represents hydrogen atom, halogen-substituted $C_{1-6}$ alkyl, halogen-substituted $C_{1-6}$ alkoxy, halogen-substituted phenyl, or halogen-substituted phenoxy, and $R^5$ represents hydrogen atom or halogen, or represents $C_{1-6}$ alkyl which may be optionally fluoro-substituted, chloro-substituted or bromo-substituted.

In the compounds of the aforementioned formula (I), more preferably $R^1$ represents methyl, ethyl, propyl or tri-fluoromethyl, $R^2$ represents methyl, ethyl, n-propyl, isopropyl, n-butyl, isobutyl, sec-butyl, tert-butyl, n-pentyl, isopentyl, sec-pentyl, tert-pentyl, n-hexyl, isohexyl, sec-hexyl, methylthiomethyl, ethylthiomethyl, methylthioethyl, ethylthioethyl, methylthiopropyl, ethylthiopropyl, methylthiobutyl, ethylthiobutyl, methylthiopentyl, ethylthiopentyl, methylsulfinylmethyl, ethylsulfinylmethyl, methylsulfinylethyl, ethylsulfinylethyl, methylsulfinylpropyl, ethylsulfinylpropyl, methylsulfinylbutyl, ethylsulfinylbutyl, methylsulfinylpentyl, ethylsulfinylpentyl, methylsulfonylmethyl, ethylsulfonylmethyl, methylsulfonylethyl, ethylsulfonylethyl, methylsulfonylpropyl, ethylsulfonylpropyl, methylsulfonylbutyl, ethylsulfonylbutyl, methylsulfonylpentyl, ethylsulfonylpentyl, or represents cyclopropyl, cyclobutyl, cyclopentyl or cyclohexyl, each of which may be optionally substituted with fluoro, chloro, bromo, methyl or ethyl, $R^3$ represents hydrogen atom, fluoro, chloro, bromo, methyl, ethyl or trifluoromethyl, $R^4$ represents fluoro, chloro or bromo, or represents methyl, ethyl, n-propyl, isopropyl, n-butyl, isobutyl, sec-butyl, tert-butyl, methoxy, ethoxy, n-propoxy or isopropoxy, each of which may be optionally partially substituted with at least one fluoro, perfluoro-substituted, or substituted with at least one fluoro and 1 or 2 chloro, $R^5$ represents hydrogen atom, fluoro, chloro or bromo, or represents methyl or ethyl, each of which may be optionally fluoro-substituted or chloro-substituted.

In the compounds of the aforementioned formula (I), further particularly preferably $R^1$ represents methyl or ethyl, $R^2$ represents isopropyl, tert-butyl, 1-methyl-2-(methylthio)ethyl, 1,1-dimethyl-2-(methylthio)ethyl, 1-methyl-2-(methylsulfinyl)ethyl, 1,1-dimethyl-2-(methylsulfinyl)ethyl, 1-methyl-2-(methylsulfonyl)ethyl or 1,1-dimethyl-2-(methylsulfonyl)ethyl, $R^3$ represents methyl, $R^4$ represents perfluoroisopropyl, and $R^5$ represents hydrogen atom.

The aforementioned preparation process (a) can be illustrated by the following reaction formula in case, for example, N-(4-heptafluoroisoproyl-2-methylphenyl)-3-methanesulfonyloxyphthalimide and isopropylamine are used as the starting materials.

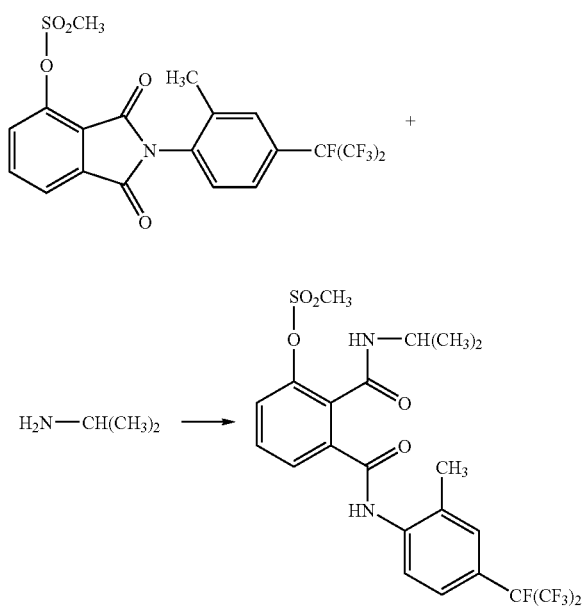

The aforementioned preparation process (b) can be illustrated by the following reaction formula in case, for example, 6-methanesulfonyloxy-N-isopropylphthalisoimide and 4-heptafluoroisopropyl-2-methylaniline are used as starting materials.

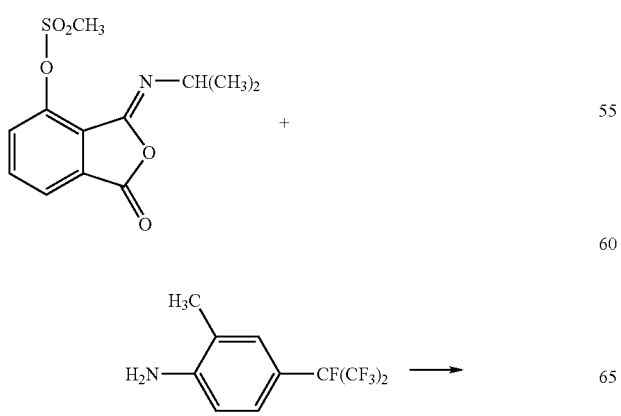

The aforementioned preparation process (c) can be illustrated by the following reaction formula in case, for example, N-(4-heptafluoroisoproyl-2-methylphenyl)-3-methanesulfonyloxyphthalisoimide and isopropylamine are used as starting materials.

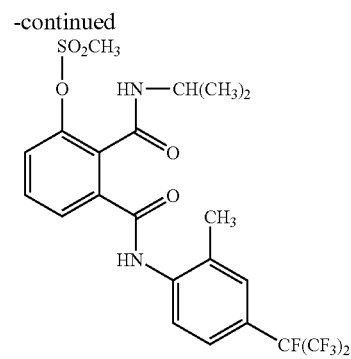

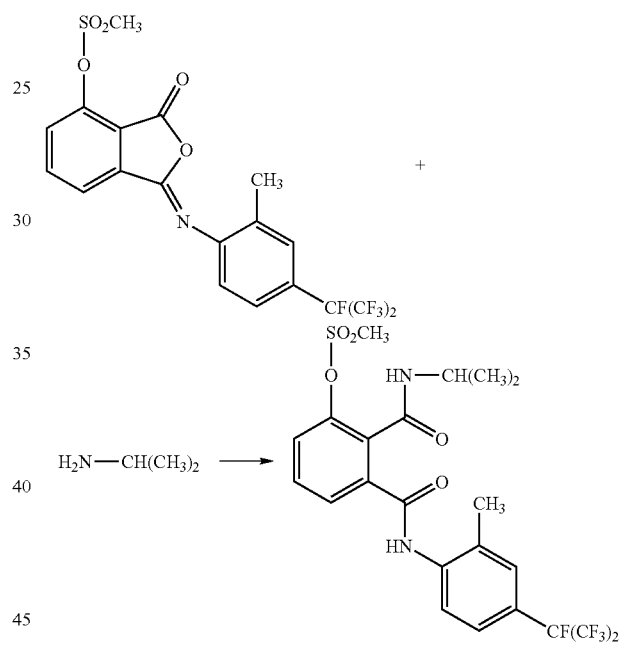

The aforementioned preparation process (d) can be illustrated by the following reaction formula in case, for example, $N^2$-[1,1-dimethyl-2-(methylthio)ethyl]-$N^1$-(4-heptafluoroisoproyl-2-methylphenyl)-3-methanesulfonyloxyphthalamide and m-chloroperbenzoic acid are used as starting materials.

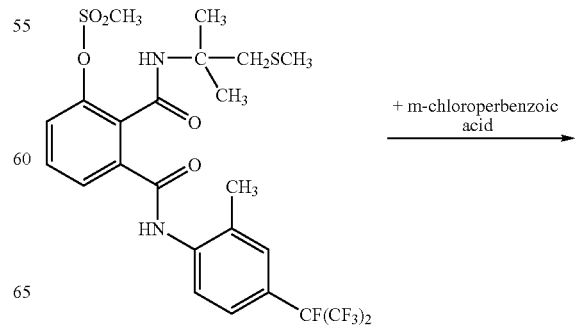

-continued

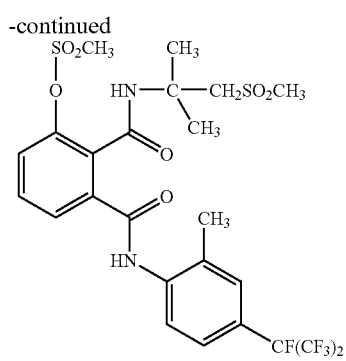

The compounds of the formula (U), the starting materials in the above-mentioned preparation process (a), are novel compounds, which are not yet described in the literature, and can be prepared, for example, by reacting compounds of the formula (VII)

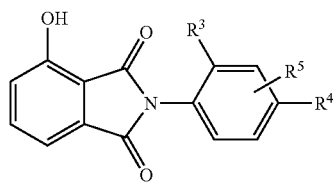
(VII)

wherein $R^3$, $R^4$ and $R^5$ have the same definitions as aforementioned, with compounds of the formula (VIII)

 (VIII)

wherein $R^1$ has the same definition as aforementioned (cf. e.g. Tetrahedron Letters 1988, 29, 5595–5598).

The compounds of the above-mentioned formula (VII), part of which are novel compounds, that are not yet described in the literature, can be prepared, for example, by reacting per se known 3-hydroxyphthalic anhydride with compounds of the aforementioned formula (V)

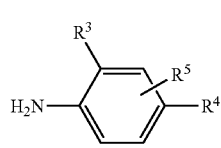
(V)

wherein $R^3$, $R^4$ and $R^5$ have the same definitions as aforementioned (cf e.g. JP 61-246161).

The compounds of the aforementioned formula (V) are known compounds and are available on the market or can be prepared by known methods (cf J. Org. Chem. 1964, 29, 1, Angew. Chem. Int. Ed. Engl., 1985, 24, 871, JP 11-302233).

The compounds of the above-mentioned formula (VIII) are compounds well known in the field of organic chemistry and as their specific examples there can be mentioned, for example, methanesulfonyl chloride, ethanesulfonyl chloride, trifluoromethanesulfonyl chloride, 2,2,2-trifluoroethanesulfonyl chloride, etc.

The compounds of the formula (II) used as the starting materials in the preparation process (a) there can be mentioned as follows:
3-methanesulfonyloxy-N-(4-trifluoromethylphenyl)phthalimide,
methanesulfonyloxy-N-(4-trifluoromethoxyphenyl)phthalimide,
3-methanesulfonyloxy-N-(4-pentafluoroethylphenyl)phthalimide,
N-(4-heptafluoroisopropylphenyl)-3-methanesulfonyloxyphthalimide,
3-methanesulfonyloxy-N-(2-methyl-4-trifluoromethylphenyl)phthalinude,
3-methanesulfonyloxy-N-(2-methyl-4-trifluoromethoxyphenyl)phthalimide,
3-methanesulfonyloxy-N-(2-methyl-4-pentafluoroethylphenyl)phthalimide,
N-(4-heptafluoroisopropyl-2-methylphenyl)-3-methanesulfonyloxyphthalimide,
3-methanesulfonyloxy-N-(2,3,4-trichlorophenyl)phthalimide,
3-ethanesulfonyloxy-N-(4-trifluoromethylphenyl)phthalimide,
3-ethanesulfonyloxy-N-(4-trifluoromethoxyphenyl)phthalimide,
3-ethanesulfonyloxy-N-(4-pentafluoroethylphenyl)phthalimide,
3-ethanesulfonyloxy-N-(4-heptafluoroisopropylphenyl)phthalimide,
3-ethanesulfonyloxy-N-(2-methyl-4-trifluoromethylphenyl)phthalimide,
3-ethanesulfonyloxy-N-(2-methyl-4-trifluoromethoxyphenyl)phthalimide,
3-ethanesulfonyloxy-N-(2-methyl-4-pentafluoroethylphenyl)phthalimide,
3-ethanesulfonyloxy-N-(4-heptafluoroisopropyl-2-methylphenyl)phthalimide,
3-ethanesulfonyloxy-N-(2,3,4-trichlorophenyl)phthalimide,
3-trifluoromethanesulfonyloxy-N-(4-trifluoromethylphenyl)phthalimide,
3-trifluoromethanesulfonyloxy-N-(4-trifluoromethoxyphenyl)phthalimide,
N-(4-pentafluoroethylphenyl)-3-trifluoromethanesulfonyloxyphthalimide,
N-(4-heptafluoroisopropylphenyl)-3-trifluoromethanesulfonyloxyphthalimide,
N-(2-methyl-4-trifluoromethylphenyl)-3-trifluoromethanesulfonyloxyphthalimide,
N-(2-methyl-4-trifluoromethoxyphenyl)-3-trifluoromethanesulfonyloxyphthalimide,
N-(2-methyl-4-pentafluoroethylphenyl)-3-trifluoromethanesulfonyloxyphthalimide,
N-(4-heptafluoroisopropyl-2-methylphenyl)-3-trifluoromethanesulfonyloxyphthalimide,
N-(2,3,4-trichlorophenyl)-3-trifluoromethanesulfonyloxyphthalimide, and so on.

The compounds of the formula (VII) used in the preparation of the aforementioned formula (II) there can be mentioned as follws:
3-hydroxy-N-(4-trifluoromethylphenyl)phthalimide,
3-hydroxy-N-(4-trifluoromethoxyphenyl)phthalimide,
3-hydroxy-N-(4-pentafluoroethylphenyl)phthalimide,
N-(4-heptafluoroisopropylphenyl)-3-hydroxyphthalimide,
3-hydroxy-N-(2-methyl-4-trifluoromethylphenyl)phthalimide,
3-hydroxy-N-(2-methyl-4-trifluoromethoxyphenyl)phthalimide, 3-hydroxy-N-(2-methyl-4-pentafluoroethylphenyl)phthalimide,
N-(4-heptafluoroisopropyl-2-methylphenyl)-3-hydroxyphthalimide,
3-hydroxy-N-(2,3,4-trichlorophenyl)phthalimide, and so on.

The compounds of the formula (V) used in the preparation of the aforementioned formula (VII) there can be mentioned as follows:
4-trifluoromethylaniline,
4-trifluoromethoxyaniline,
4-pentafluoroethylaniline,
4-heptafluoroisopropylaniline,
2-methyl-4-trifluoromethylaniline,
2-methyl-4-trifluoromethoxyaniline,
2-methyl-4-pentafluoroethylaniline,
4-heptafluoroisopropyl-2-methylaniline,
2,3,4-trichloroaniline, and so on.

The compounds of the formula (III), the starting materials in the above-mentioned preparation process (a), are compounds well known in the field of organic chemistry and can be prepared according to the process described in DE-A 20 45 905, WO 01/23350 Pamphlet, etc.

The compounds of the formula (III) used as the starting materials in the preparation process (a) there can be mentioned as follows:
n-propylamine,
isopropylamine,
n-butylamine,
sec-butylamine,
isobutylamine,
tert-butylamine,
tert-amylamine,
cyclopropylamine,
cyclopentylamine,
cyclohexylamine,
2-(methylthio)ethylamine,
2-(ethylthio)ethylamine,
1-methyl-2-(methylthio)ethylamine,
1,1-dimethyl-2-(methylthio)ethylamine, and so on.

The compounds of the formula (IV), the starting materials in the above-mentioned preparation process (b), are novel compounds which are not described in the literature yet and can be prepared by reacting compounds of the formula (IX)

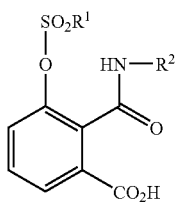

(IX)

wherein $R^1$ and $R^2$ have the same definitions as aforementioned, in the presence of a condensing agent or an acid binding agent (cf. e.g. J. Med. Chem. 1967, 10, 982)

The compounds of the above-mentioned formula (IX) are also novel compounds which are not yet described in the literature and can be prepared by reacting compounds of the formula (X)

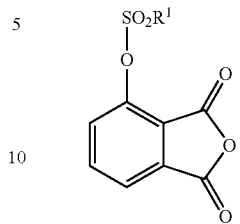

(X)

wherein $R^1$ has the same definition as aforementioned with compounds of the formula (III)

$$H_2N-R^2 \quad (III)$$

wherein $R^2$ has the same definition as aforementioned (cf. e.g. J. Org. Chem. 1981, 46, 175).

The compounds of the above-mentioned formula (X) are also novel compounds which are not yet described in the literature and can be prepared by reacting the per se known 3-hydroxyphthalic anhydride with compounds of formula (VIII)

$$R^1SO_2Cl \quad (VIII)$$

wherein $R^1$ has the same definition as aforementioned (cf. e.g. Tetrahedron Lett. 1988, 29, 5595–5598).

The compounds of the formula (IV) used as starting materials in the preparation process (b) there can be mentioned as follows:
6-methanesulfonyloxy-N-n-propylphthalisoimide,
N-isopropyl-6-methanesulfonyloxyphthalisoimide,
N-n-butyl-6-methanesulfonyloxyphthalisoimide,
N-sec-butyl-6-methanesulfonyloxyphthalisoimide,
N-isobutyl-6-methanesulfonyloxyphthalisoimide,
N-tert-butyl-6-methanesulfonyloxyphthalisoimide,
6-methanesulfonyloxy-N-[2-(methylthio)ethyl]phthalisoimide,
N-[2-(ethylthio)ethyl]-6-methanesulfonyloxyphthalisoimide,
6-methanesulfonyloxy-N-[1-methyl-2-(methylthio)ethyl]phthalisoimide,
N-[1,1-dimethyl-2-(methylthio)ethyl]-6-methanesulfonyloxyphthalisoimide,
6-ethanesulfonyloxy-N-n-propylphthalisoimide,
6-ethanesulfonyloxy-N-isopropylphthalisoimide,
N-n-butyl-6-ethanesulfonyloxyphthalisoimide,
N-sec-butyl-6-ethanesulfonyloxyphthalisoimide,
6-ethanesulfonyloxy-N-isobutylphthalisoimide,
N-tert-butyl-6-ethanesulfonyloxyphthalisoimide,
6-ethanesulfonyloxy-N-[2-(methylthio)ethyl]phthalisoimide,
6-ethanesulfonyloxy-N-[2-(ethylthio)ethyl]phthalisoimide,
6-ethanesulfonyloxy-N-[1-methyl-2-(methylthio)ethyl]phthalisoimide,
N-[1,1-dimethyl-2-(methylthio)ethyl]-6-ethanesulfonyloxyphthalisoimide,
N-n-propyl-6-trifluoromethanesulfonyloxyphthalisoimide,
N-isopropyl-6-trifluoromethanesulfonyloxyphthalisoimide,
N-n-butyl-6-trifluoromethanesulfonyloxyphthalisoimide,
N-sec-butyl-6-trifluoromethanesulfonyloxyphthalisoimide,
N-isobutyl-6-trifluoromethanesulfonyloxyphthalisoimide,
N-tert-butyl-6-trifluoromethanesulfonyloxyphthalisoimide, N-[2-(methylthio)ethyl]-6-trifluoromethanesulfonyloxyphthalisoimide,
N-[2-(ethylthio)ethyl]-6-trifluoromethanesulfonyloxyphthalisoimide,
N-[1-methyl-2-(methylthio)ethyl]-6-trifluoromethanesulfonyloxyphthalisoimide,
N-[1,1-dimethyl-2-(methylthio)ethyl]-6-trifluoromethanesulfonyloxyphthalisoimide, and so on.

The compounds of the formula (IX) used in the preparation of the aforementioned formula (IV) there can be mentioned as follows:
3-methanesulfonyloxy-N-n-propylphthalamic acid,
N-isopropyl-3-methanesulfonyloxyphthalamic acid,
N-n-butyl-3-methanesulfonyloxyphthalamic acid,
N-sec-butyl-3-methanesulfonyloxyphthalamic acid,
N-isobutyl-3-methanesulfonyloxyphthalamic acid,
N-t-butyl-3-methanesulfonyloxyphthalamic acid,
3-methanesulfonyloxy-N-[2-(methylthio)ethyl]phthalamic acid,
N-[2-(ethylthio)ethyl]-3-methanesulfonyloxyphthalamic acid,
3-methanesulfonyloxy-N-[1-methyl-2-(methylthio)ethyl]phthalamic acid,
N-[1,1-di-methyl-2-(methylthio)ethyl]-3-methanesulfonyloxyphthalamic acid,
3-ethanesulfonyloxy-N-n-propylphthalamic acid,
3-ethanesulfonyloxy-N-isopropylphthalamic acid,
N-n-butyl-3-ethanesulfonyloxyphthalamic acid,
N-sec-butyl-3-ethanesulfonyloxyphthalamic acid,
3-ethanesulfonyloxy-N-isobutylphthalamic acid,
N-t-butyl-3-ethanesulfonyloxyphthalamic acid,
3-ethanesulfonyloxy-N-[2-(methylthio)ethyl]phthalamic acid,
3-ethanesulfonyloxy-N-[2-(ethylthio)ethyl]phthalamic acid,
3-ethanesulfonyloxy-N-[1-methyl-2-(methylthio)ethyl]phthalamic acid,
N-[1,1-di-methyl-2-(methylthio)ethyl]-3-ethanesulfonyloxyphthalamic acid,
N-n-propyl-3-trifluoromethanesulfonyloxyphthalamic acid,
N-isopropyl-3-trifluoromethanesulfonyloxyphthalamic acid,
N-n-butyl-3-trifluoromethanesulfonyloxyphthalamic acid,
N-sec-butyl-3-trifluoromethanesulfonyloxyphthalamic acid,
N-isobutyl-3-trifluoromethanesulfonyloxyphthalamic acid,
N-t-butyl-3-trifluoromethanesulfonyloxyphthalamic acid,
N-[2-(methylthio)ethyl]-3-trifluoromethanesulfonyloxyphthalamic acid,
N-[2-(ethylthio)ethyl]-3-trifluoromethanesulfonyloxyphthalamic acid,
N-[1-methyl-2-(methylthio)ethyl]-3-trifluoromethanesulfonyloxyphthalamic acid,
N-[1,1-dimethyl-2-(methylthio)ethyl]-3-trifluoromethanesulfonyloxyphthalamic acid, and so on.

As the specific examples of the condensing agent or acid binding agent used in the preparation of the compounds of the aforementioned formula (IX) there can be mentioned as follows:

As condensing agent there can be mentioned, for example, Mukaiyama's reagent (2-chloro-N-methylpyridinium iodide), DCC (1,3-dicyclohexylcarbodiimide), CDI (carbonyl diimidazole), trifluoroacetic anhydride, methyl chlorocarbonate, and so on.

As acid binding agent there can be mentioned, for example, as organic base, tertiary amines, dialkylaminoanilines and pyridines, for example, triethylamine, 1,1,4,4-tetramethylethylenediamine (TMEDA), N,N-dimethylaniline, N,N-diethylaniline, pyridine, 4-dimethylaminopyridine (DMAP), etc.; as inorganic base, hydroxides, carbonates, bicarbonates, etc. of alkali metals and alkaline earth metals, for example, sodium hydrogen carbonate, potassium hydrogen carbonate, sodium carbonate, potassium carbonate, lithium hydroxide, sodium hydroxide, potassium hydroxide, and so on.

The compounds of the formula (X) used in the preparation of the aforementioned formula (IX) there can be mentioned as follows:
3-methanesulfonyloxyphthalic anhydride,
3-ethanesulfonyloxyphthalic anhydride,
3-trifluoromethanesulfonyloxyphthalic anhydride,
3-(2,2,2-trifluoroethane)sulfonyloxyphthalic anhydride, and so on.

The compounds of the formula (VI), the starting materials in the above-mentioned preparation process (c), are novel compounds which are not yet described in the literature and can be prepared by reacting compounds of the formula (XI).

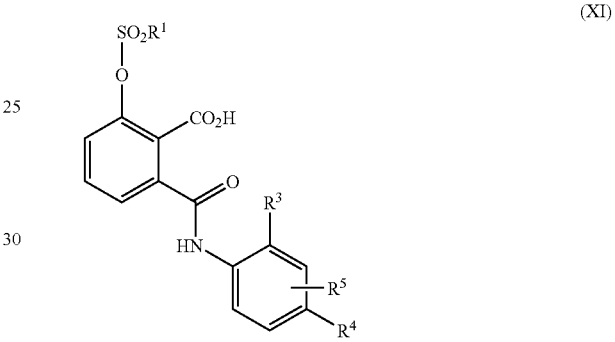

(XI)

wherein $R^1$, $R^3$, $R^4$ and $R^5$ have the same definitions as aforementioned in the presence of such a condensing agent or an acid binding agents as aforementioned (cf. e.g. J. Med. Chem. 1967, 10, 982).

The compounds of the above-mentioned formula (XI) are also novel compounds which are not yet described in the literature and can be prepared by reacting compounds of the formula (X)

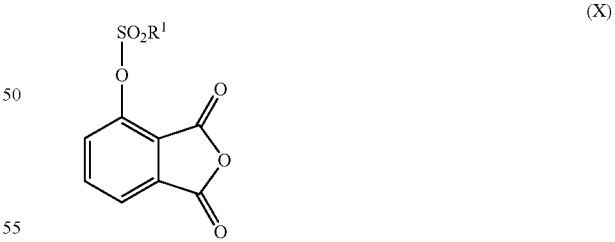

(X)

wherein $R^1$ has the same definition as aforementioned with compounds of the formula (III)

$$H_2N-R^2 \qquad (III)$$

wherein $R^2$ has the same definition as aforementioned (cf. e.g. J. Org. Chem. 1981, 46, 175).

The compounds of the formula (VI) used as starting materials in the above-mentioned preparation process (c) there can be mentioned as follws:

3-methanesulfonyloxy-N-(4-trifluoromethylphenyl)phthalisoimide,
3-methanesulfonyloxy-N-(4-trifluoromethoxyphenyl)phthalisoimide,
3-methanesulfonyloxy-N-(4-pentafluoroethylphenyl)phthalisoimide,
N-(4-heptafluoroisopropylphenyl)-3-methanesulfonyloxyphthalisoimide,
N-(4-heptafluoroisopropyl-2-methylphenyl)-3-methanesulfonyloxyphthalisoimide,
3-methanesulfonyloxy-N-(2,3,4-trichlorophenyl)phthalisoimide,
3-ethanesulfonyloxy-N-(4-trifluoromethylphenyl)phthalisoimide,
3-ethanesulfonyloxy-N-(4-trifluoromethoxyphenyl)phthalisoimide,
3-ethanesulfonyloxy-N-(4-pentafluoroethylphenyl)phthalisoimide,
3-ethanesulfonyloxy-N-(4-heptafluoroisopropylphenyl)phthalisoimide,
3-ethanesulfonyloxy-N-(4-heptafluoroisopropyl-2-methylphenyl)phthalisoimide,
3-ethanesulfonyloxy-N-(2,3,4-trichlorophenyl)phthalisoimide,
3-trifluoromethanesulfonyloxy-N-(4-trifluoromethylphenyl)phthalisoimide,
3-trifluoromethanesulfonyloxy-N-(4-trifluoromethoxyphenyl)phthalisoimide,
N-(4-pentafluoroethylphenyl)-3-trifluoromethanesulfonyloxyphthalisoimide,
N-(4-heptafluoroisopropylphenyl)-3-trifluoromethanesulfonyloxyphthalisoimide,
N-(4-heptafluoroisopropyl-2-methylphenyl)-3-trifluoromethanesulfonyloxyphthalisoimide,
N-(2,3,4-trichlorophenyl)-3-methanesulfonyloxyphthalisoimide, etc.

The compounds of the formula (XI) used in the preparation of the aforementioned formula (VI) there can be mentioned as follows:
6-methanesulfonyloxy-N-(4-trifluoromethylphenyl)phthalamic acid,
6-methanesulfonyloxy-N-(4-trifluoromethoxyphenyl)phthalamic acid,
6-methanesulfonyloxy-N-(4-pentafluoroethylphenyl)phthalamic acid,
N-(4-heptafluoroisopropylphenyl)-6-methanesulfonyloxyphthalamic acid,
N-(4-heptafluoroisopropyl-2-methylphenyl)-6-methanesulfonyloxyphthalamic acid,
6-methanesulfonyloxy-N-(2,3,4-trichlorophenyl)phthalamic acid,
6-ethanesulfonyloxy-N-(4-trifluoromethylphenyl)phthalamic acid,
6-ethanesulfonyloxy-N-(4-trifluoromethoxyphenyl)phthalamic acid,
6-ethanesulfonyloxy-N-(4-pentafluoroethylphenyli)phthalamic acid,
6-ethanesulfonyloxy-N-(4-heptafluoroisopropylphenyl)phthalamic acid,
6-ethanesulfonyloxy-N-(4-heptafluoroisopropyl-2-methylphenyl)phthalamic acid,
6-ethanesulfonyloxy-N-(2,3,4-trichlorophenyl)phthalamic acid,
6-trifluoromethanesulfonyloxy-N-(4-trifluoromethylphenyl)phthalamic acid,
6-trifluoromethanesulfonyloxy-N-(4-trifluoromethoxyphenyl)phthalamic acid,
N-(4-pentafluoroethylphenyl)-6-trifluoromethanesulfonyloxyphthalamic acid,
N-(4-heptafluoroisopropylphenyl)-6-trifluoromethanesulfonyloxyphthalamic acid,
N-(4-heptafluoroisopropyl-2-methylphenyl)-6-trifluoromethanesulfonyloxyphthalamic acid,
N-(2,3,4-trichlorophenyl)-3-trifluoromethanesulfonyloxyphthalamic acid, and so on.

The compounds of the formula (Id), the starting materials in the above-mentioned preparation process (d), correspond to the compounds of the formula (I) of the present invention, in which $R^2$ is alkylthioalkyl, and can be prepared, for example, according to the aforementioned preparation processes (a) to (c).

The compounds of the formula (Id) used as starting materials in the above-mentioned preparation process (d) there can be mentioned as follows:
$N^2$-[1-methyl-2-(methylthio)ethyl]-$N^1$-(4-trifluoromethoxy-2-methylphenyl)-3-methanesulfonyloxyphthalamide,
$N^1$-(4-heptafluoroisopropylphenyl)-$N^2$-[1-methyl-2-(methylthio)ethyl]-3-methanesulfonyloxyphthalamide,
$N^1$-(4-heptafluoroisoprppyl-2-methylphenyl)-$N^2$-[1-methyl-2-(methylthio)ethyl]-3-methanesulfonyloxyphthalamide,
$N^1$-(4-heptafluoroisopropyl-2-methylphenyl)-$N^2$-[1-methyl-2-(methylthio)ethyl]-3-ethanesulfonyloxyphthalamide,
$N^1$-(4-heptafluoroisopropyl-2-methylphenyl)-$N^2$-[1-methyl-2-(methylthio)ethyl]-3-trifluoromethanesulfonyloxyphthalamide,
$N^2$-[1,1-dimethyl-2-(methylthio)ethyl]-$N^1$-(4-heptafluoroisopropyl-2-methylphenyl)-3-methanesulfonyloxyphthalamide,
$N^2$-[1,1-dimethyl-2-(methylthio)ethyl]-$N^1$-(4-heptafluoroisopropyl-2-methylphenyl)-3-ethanesulfonyloxyphthalamide,
$N^2$-[1,1-dimethyl-2-(methylthio)ethyl]-$N^1$-(2,3,4-trichlorophenyl)-3-methanesulfonyloxyphthalamide, and so on.

As the oxidizing agent used for S-oxidation of the compounds of the formula (Id) in the preparation process (d) there can be mentioned, for example, m-chloroperbenzoic acid, peracetic acid, potassium metaperiodate, potassium hydrogen persulfate (trade name: OXONE$^R$), hydrogen peroxide, and so on.

The compounds of the formula (II), formula (IV), formula (VI), formula (IX), formulae (X) and (IX), either starting materials or intermediate products in the aforementioned processes (a) to (c) for the preparation of the compounds of the formula (I) of the present invention are all novel compounds which are not described in the literature yet and are represented collectively by the following general formula (XII)

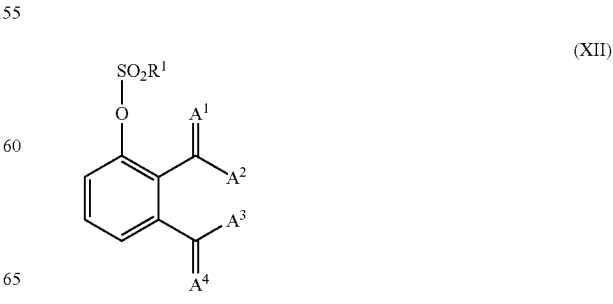

wherein
R¹ has the same definition as aforementioned,
(a) A¹ and A⁴ each represents oxygen atom,
A² represents the group NH—R² and A³ represents hydroxy,
or
A² represents hydroxy and A³ represents the group

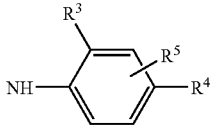

or
A², together with A³, represents a group selected from

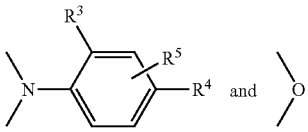 and 

(b) A¹ represents the group N—R²,
A², together with A³, represents the group

and
A⁴ represents oxygen atom,
or
(c) A¹ represents oxygen atom,
A², together with A³, represents the group

and
A⁴ represents the group

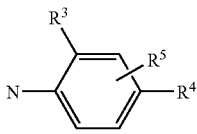

wherein R², R³, R⁴ and R⁵ have the same definition as aforementioned.

The reaction of the aforementioned preparation process (a) can be conducted in an adequate diluent. As examples of the diluent used in that case there can be mentioned aliphatic, alicyclic and aromatic hydrocarbons (may be optionally chlorinated), for example, pentane, hexane, cyclohexane, petroleum ether, ligroine, benzene, toluene, xylene, dichloromethane, chloroform, carbon tetrachloride, 1,2-dichloroethane, chlorobenzene, dichlorobenzene, etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM), etc.; esters, for example, ethyl acetate, amyl acetate, etc.; acid amides, for example, dimethylformamide (DMF), dimethylacetamide (DMA), N-methylpyrrolidone, 1,3-dimethyl-2-imidazolidinone, hexamethyl phosphoric triamide (HMPA), etc.

The preparation process (a) can be conducted in the presence of a base and as examples of said base there can be mentioned, for example, tertiary amines, dialkylaminoanilines and pyridines, for example, triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2.2.2]octane (DABCO), 1,8-diazabicyclo[5.4.0]undec-7-ene (DBU), etc.

The preparation process (a) can be conducted in a substantially wide range of temperature. However, it can be conducted at the temperatures in a range of generally about −20 to about 150° C., preferably about 10 to about 100° C. Although said reaction is conducted desirably under normal pressure, it can be operated also under elevated pressure or under reduced pressure.

In conducting the preparation process (a), the aimed compounds of the formula (I) can be obtained, for example, by reacting 1 to 25 mole amount of the compounds of the formula (III) to 1 mole of the compounds of the formula (II).

The reaction of the aforementioned preparation process (b) can be conducted in an adequate diluent, either singly or mixed. As examples of the diluent used in that case there can be mentioned water; aliphatic, alicyclic and aromatic hydrocarbons (may be optionally chlorinated), for example, pentane, hexane, cyclohexane, petroleum ether, ligroine, benzene, toluene, xylene, dichloromethane, chloroform, carbon tetrachloride, 1,2-dichloroethane, chlorobenzene, dichlorobenzene, etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM), etc.; nitriles, for example, acetonitrile, propionitrile, acrylonitrile, etc.; esters, for example, ethyl acetate, amyl acetate, etc.

The preparation process (b) can be conducted in the presence of an acid catalyst and as examples of said acid catalyst there can be mentioned mineral acids, for example, hydrochloric acid, sulfuric acid, etc.; organic acids, for example, acetic acid, trifluoroacetic acid, propionic acid, methanesulfonic acid, benzenesulfonic acid, p-toluenesulfonic acid, etc.

The preparation process (b) can be conducted in a substantially wide range of temperature. However, it can be conducted at the temperatures in a range of generally about −20 to about 100° C., preferably about 0 to about 100° C. Although said reaction is conducted desirably under normal pressure, it can be operated also under elevated pressure or under reduced pressure.

In conducting the preparation process (b), the aimed compounds of the formula (I) can be obtained, for example, by reacting 1 to 1.5 mole amount of the compounds of the formula (V) to 1 mole of the compounds of the formula (IV) in a diluent, for example, acetonitrile.

In conducting the preparation process (b), the compound of the formula (I) can be obtained also by conducting reactions continuously in one pot, starting from 3-hydroxyphthalic anhydride without isolating the compounds of the formula (X), the compounds of the formula (IX) and the compounds of the formula (IV).

The reaction of the aforementioned preparation process (c) can be conducted in an adequate diluent, either singly or mixed. As examples of the diluent used in that case there can be mentioned water; aliphatic, alicyclic and aromatic hydrocarbons (may be optionally chlorinated), for example, pentane, hexane, cyclohexane, petroleum ether, ligroine, benzene, toluene, xylene, dichloromethane, chloroform, carbon tetrachloride, 1,2-dichloroethane, chlorobenzene, dichlorobenzene, etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM), etc.; nitriles, for example, acetonitrile, propionitrile, acrylonitrile etc.; esters, for example, ethyl acetate, amyl acetate, etc.

The preparation process (c) can be conducted in the presence of an acid catalyst and as examples of said acid catalyst there can be mentioned rmineral acids, for example, hydrochloric acid, sulfuric acid, etc.; organic acids, for example, acetic acid, trifluoroacetic acid, propionic acid, methanesulfonic acid, benzenesulfonic acid, p-toluenesulfonic acid, etc.

The preparation process (c) can be conducted in a substantially wide range of temperature. However, it can be conducted at the temperatures in a range of generally about −20 to about 100° C., preferably about 0 to about 100° C. Although said reaction is conducted desirably under normal pressure, it can be operated also under elevated pressure or under reduced pressure.

In conducting the preparation process (c), the aimed compounds of the formula (I) can be obtained, for example, by reacting 1–2 mole amount of the compounds of the formula (III) to 1 mole of the compounds of the formula (VI) in a diluent, for example, acetonitrile.

In conducting the preparation process (c), the compounds of the formula (I) can be obtained also by continuously conducting reactions in one pot, starting from 3-hydroxyphthalic anhydride without isolating the compounds of the formula (X), the compounds of the formula (XI) and the compounds of the formula (VI).

The reaction of the aforementioned preparation process (d) can be conducted in an adequate diluent. As examples of the diluent used in that case there can be mentioned water; aliphatic, alicyclic and aromatic hydrocarbons (may be optionally chlorinated), for example, benzene, toluene, xylene, dichloromethane, chloroform, carbon tetrachloride, 1,2-dichloroethane, chlorobenzene, dichlorobenzene, etc.; alcohols, for example, methanol, ethanol, isopropanol, butanol, etc.; acids, for example, formic acid, acetic acid, etc.

The preparation process (d) can be conducted in a substantially wide range of temperature. However, it can be conducted at the temperatures in a range of generally about −50 to about 150° C., preferably about −10 to about 100° C. Although said reaction is conducted desirably under normal pressure, it can be operated also under elevated pressure or under reduced pressure.

In conducting the preparation process (d), the aimed compounds of the aforementioned formula (I), in case $R^2$ represents alkylsulfinylalkyl or alkylsulfonylalkyl, can be obtained, for example, by reacting 1–5 mole amount of an oxidizing agent, for example, m-chloroperbenzoic acid to 1 mole of a compound of the formula (Id) in a diluent, for example, dichloromethane.

The compounds of the formula (I) of the present invention show strong insecticidal action. They can, therefore, be used as insecticidal agents. And the active compounds of the formula (I) of the present invention exhibit exact controlling effect against harmful insects without phytotoxicity against cultured plants. The compounds of the present invention can be used for controlling a wide variety of pests, for example, harmful sucking insects, biting insects and other plant-parasitic pests, stored grain pests, hygienic pests, etc. and applied for their extermination.

As examples of such pests there can be mentioned the following pests:

As insects, there can be mentioned coleoptera, for example,

*Callosobruchus Chinensis, Sitophilus zeamais, Tribolium castaneum, Epilachna vigintioctomaculata, Agriotes fuscicollis, Anomala rufocuprea, Leptinotarsa decemlineata, Diabrotica* spp., *Manochamus alternatus, Lissorhoptrus oryzophilus, Lyctus bruneus;*

Lepidoptera, for example,

*Lymantria dispar, Malacosoma neustria, Pieris rapae, Spodoptera litura, Mamestra brassicae, Chilo suppressalis, Pyrausta nubilalis, Ephestia cautella, Adoxophyes orana, Carpocapsa pomonella, Agrotis fucosa, Galleria mellonella, Plutella maculipennis, Heliothis virescens, Phyllocnistis citrella;*

Hemiptera, for example,

*Nephotettix cincticeps, Nilaparvata lugens, Pseudococcus comstocki, Unaspis yanonensis, Myzus persicae, Aphis pomi, Aphis gossypii, Rhopalosiphum pseudobrassicas, Stephanitis nashi, Nazara* spp., *Cimex lectularius, Trialeurodes vaporariorum, Psylla* spp.;

Orthoptera, for example,

*Blatella germanica, Periplaneta americana, Gryllotalpa africana, Locusta migratoria* migratoriodes;

Homoptera, for example,

*Reticulitermes speratus, Coptoternes formosanus;*

Diptera, for example,

*Musca domestica, Aedes aegypti, Hylemia platura, Culex pipiens, Anopheles slnensis, Culex tritaeniorhynchus*, etc.

Moreover, as mites there can be mentioned, for example,

*Tetranychus telarius, Tetranychus urticae, Panonychus citri, Aculops pelekassi, Tarsonemus* spp. etc.

Furthermore, as nematodes there can be mentioned, for example,

*Meloidogyne incognita, Bursaphelenchus lignicolus Mamiya* et *Kiyohara, Aphelenchoides basseyi, Heterodera glycines, Pratylenchus* spp. etc.

In addition, in the field of veterinary medicine, the novel compounds of the present invention can be effectively used against various harmful animal-parasitic pests (endoparasites and ectoparasites), for example, insects and helminthes. As examples of such animal-parasitic pests there can be mentioned the following pests:

As insects there can be mentioned, for example,

*Gastrophilus* spp., *Stomoxys* spp., *Trichodectes* spp., *Rhodnius* spp., *Ctenocephalides canis*, etc.

As mites there can be mentioned, for example,

*Ornithodoros* spp., *Ixodes* spp., *Boophilus* spp., etc.

In the present invention substances having insecticidal action against pests, which include all of them; are in some cases called collectively as insecticides The active compounds of the present invention can be made into customary formulation forms, when they are used as insecticides. As formulation forms there can be mentioned, for example, solutions, emulsions, wettable powders, water dispersible granules, suspensions, powders, foaming agents, pastes, tablets, granules, aerosols, active compound-impregnated natural and synthetic substances, microcapsules, seed coating agents, formulations used with burning equipment (as burning equipment, for example, fumigation and smoking cartridges, cans, coils, etc.), ULV [cold mist, warm mist], etc.

These formulations can be prepared according to per se known methods, for example, by mixing the active compounds with extenders, namely liquid diluents; liquefied gas diluents; solid diluents or carriers, and optionally by using surface-active agents, namely emulsifiers and/or dispersants and/or foam-forming agents.

In case water is used as extender, for example, organic solvents can be used also as auxiliary solvents.

As liquid diluents or carriers there can be mentioned, for example, aromatic hydrocarbons (for example, xylene, toluene, alkylnaphthalene etc.), chlorinated aromatic or chlorinated aliphatic hydrocarbons (for example, chlorobenzenes, ethylene chlorides, methylene chloride, etc.), aliphatic hydrocarbons [for example, cyclohexane etc. or paraffins (for example, mineral oil fractions etc.)], alcohols (for example, butanol, glycols and their ethers, esters, etc.), ketones (for example, acetone, methyl ethyl ketone, methyl isobutyl ketone, cyclohexanone, etc.), strongly polar solvents (for example, dimethylformamide, dimethyl sulfoxide, etc.), and water.

Liquefied gas diluents or carriers are substances that are gases at normal temperature and pressure and there can be mentioned, for example, aerosol propellants such as butane, propane, nitrogen gas, carbon dioxide, halogenated hydrocarbons.

As solid diluents there can be mentioned, for example, ground natural minerals (for example, kaolin, clay, talc, chalk, quartz, attapulgite, montmorillonite, diatomaceous earth, etc.), ground synthetic minerals (for example, highly dispersed silicic acid, alumina, silicates, etc.).

As solid carriers for granules there can be mentioned, for example, crushed and fractionated rocks (for example, calcite, marble, pumice, sepiolite, dolomite, etc.) synthetic granules of inorganic and organic meals, particles of organic materials (for example, saw dust, coconut shells, maize cobs, tobacco stalks etc.) etc.

As emulsifiers and/or foam-forming agents there can be mentioned, for example, nonionic and anionic emulsifiers [for example, polyoxyethylene fatty acid esters, polyoxyethylene fatty acid alcohol ethers (for example, alkylaryl polyglycol ethers, alkylsulfonates, alkylsulfates, arylsulfonates, etc.)], albumin hydrolysis products, etc.

Dispersants include, for example, lignin sulfite waste liquor and methyl cellulose.

Tackifiers can also be used in formulations (powders, granules, emulsifiable concentrates). As said tackifiers there can be mentioned, for example, carboxymethyl cellulose, natural and synthetic polymers (for example, gum Arabic, polyvinyl alcohol, polyvinyl acetate, etc.).

Colorants can also be used. As said colorants there can be mentioned, for example, inorganic pigments (for example, iron oxide, titanium oxide, Prussian Blue etc,), organic dyestuffs such as alizarin dyestuffs, azo dyestuffs or metal phthalocyanine dyestuffs, and further traces nutrients such as salts of iron, manganese, boron, copper, cobalt, molybdenum and zinc.

Said formulations can contain the aforementioned active components of the amount in the range of generally 0.1–95% by weight, preferably 0.5–90% by weight.

The active compounds of the formula (I) of the present invention can exist also as a mixed agent with other active compounds, for example, insecticides, poisonous baits, bactericides, miticides, nematicides, fungicides, growth regulators or herbicides in the form of their commercially useful formulations or in the application forms prepared from such formulations. Here, as the above-mentioned insecticides, there can be mentioned, for example, organophosphorous agents, carbamate agents, carboxylate type chemicals, chlorinated hydrocarbon type chemicals, insecticidal substances produced by microbes, etc.

Particularly advantageous co-components are, for example, the following:

Fungicides:

2-phenylphenol; 8-hydroxyquinoline sulfate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-s; bromuconazole; bupirimate; buthiobate; butylamine; calcium polysulfide; capsimycin; captafol; captan; carbendazim; carboxin; carpropamid; carvone; chinomethionate; chlobenthiazone; chlorfenazole; chloroneb; chlorothalonil; chlozolinate; clozylacon; cyazofamide; cyflufenamide; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-m; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-al; fosetyl-sodium; fuberidazole; furalaxyl; furametpyr; furcarbanil; furmecyclox; guazatine; hexachlorobenzene; hexaconazole; hymexazol; imazalil; imibenconazole; iminoctadine triacetate; iminoctadine tris(albesilate); iodocarb; ipconazole; iprobenfos; iprodione; iprovalicarb; irumamycin; isoprothiolane; isovaledione; kasugamycin; kresoximmethyl; mancozeb; maneb; meferimzone; mepanipyrim; mepronil; metalaxyl; metalaxyl-m; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazol; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolnitrine; quinconazole; quinoxyfen; quintozene; simeconazole; spiroxamine; sulfur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin a; vinclozolin; zineb; ziram; zoxamide; (2S)-N-[2-[4-[[3-(4-chlorophenyl)-2-propinyl] oxy]-3-methoxyphenyl]ethyl]-3-methyl-2-[(methylsulfonyl)amino]-butanamide; 1-(1-naphthalenyl)-1H-pyrrol-2, 5-dione; 2,3,5,6-tetrachloro-4-(methylsulfonyl)-pyridine;

2-amino-4-methyl-n-phenyl-5-thiazolcarboxamide; 2-chloro-N-(2,3-dihydro-1,1,3-trimethyl-1H-inden-4-yl)-3-pyridincarboxamide; 3,4,5-trichloro-2,6-pyridindicarbonitrile; actinovate; cis-1-(4-chlorophenyl)-2-(1H-1,2, 4triazol-1-yl)-cycloheptanol; methyl-1-(2,3-dihydro-2,2-dimethyl-1H-inden-1-yl)-1-Himidazol-5-carboxylate; mono-potassium carbonate; n-(6-methoxy-3-pyridinyl)-cyclopropancarboxamide; n-butyl-8-(1,1-dimethylethyl)-1-oxaspiro[4.5]decan-3-amine; sodium trathiocarbonate; and copper salts and preparations, such as: Bordeaux mixture, copper hydroxide, copper naphthenate, copper oxychloride, copper sulphate, cufraneb, copper oxide, mancopper, oxine-copper.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/acaricides/nematicides:
abamectin, ABG-9008, acephate, acequinocyl, acetamiprid, acetoprole, acrinathrin, AKD-1022, AKD-3059, AKD-3088, alanycarb, aldicarb, aldoxycarb, allethrin, allethrin 1R-isomers, alpha-cypermethrin (alphamethrin), amitraz, avermectin, AZ 60541, azadirachtin, azamethiphos, azinphos-methly, azinphos-ethyl, azocyclotin, *Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, Baculoviruses, *Beauveria bassiana, Beauveria tenella*, bendiocarb, benfuracarb, bensultap, benzoximate, beta-cyfluthrin, betacypermethrin, bifenazate, bifenthrin, binapacryl, bioallethrin, bioallethrin-S-cyclopentyl-isomer, bioethanomethrin, biopermethrin, bioresmethrin, bistrifluron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben,
cadusafos, camphechlor, carbaryl, carbofuran, carbophenothion, carbosulfan, cartap, CGA-50439, chinomethionat, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothianidine, clothiazoben, codlemone, coumaphos, cyanofenphos, cyanophos, cycloprene, cycloprothrin, *Cydia pomonella*, cyfluthrin, cyhalothrin, cyhexatin, cypermethrin, cyphenothrin (1R-trans-isomer), cyromazine, DDT, deltamethrin, demeton-S-methyl, demeton-S-methylsulphon, diafenthiuron, dialifos, diazinon, dichlofenthion, dichlorvos, dicofol, dicrotophos, dicyclanil, diflubenzuron, dimethoate, dimethylvinphos, dinobuton, dinocap, dinetofuran, diofenolan, disulfoton, docusat-sodium, dofenapyn, DOWCO-439,
eflusilanate, emamectin, emarnectin-benzoate, empenthrin (1R-isomer), endosulfan, *Entomopthora* spp., EPN, esfenvalerate, ethiofencarb, ethiprole, ethion, ethoprophos, etofenprox, etoxazole, etrimfos,
famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb,
Gamma-HCH, gossyplure, grandlure, granulosis viruses,
halfenprox, halofenozide, HCH, HCN-801, heptenophos, hexaflumuron, hexythiazox, hydramethylnone, hydroprene,
IKA-2002, imidacloprid, imiprothrin, indoxacarb, iodofenphos, iprobenfos, isazofos, isofenphos, isoprocarb, isoxathion, ivermectin, Japonilure,
kadethrin, kempolyederviren, kinoprene, lambda-cyhalothrin, lindane, lufenuron, malathion, mecarbam, mesulfenfos, metaldehyd, metam-sodium, methacrifos, methamidophos, metharhizium anisopliae, metharhizium flavoviride, methidathion, methiocarb, methomyl, methoprene, methoxychlor, methoxyfenozide, metolcarb, metoxadiazone, mevinphos, milbemectin, milbemycin, MKI-245, MON-45700, monocrotophos, moxidectin, MTI-800,
Naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron,
OK-5101, OK-5201, OK-9601, OK-9602, OK-9701, OK-9802, omethoate, oxamyl, oxydemeton-methyl,
paecilomyces fumosoroseus, parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, prallethrin, profenofos, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen,
quinalphos, resmethrin, RH-5849, ribavirin, RU-12457, RU-15525,
S-421, S-1833, salithion, sebufos, SI-0009, silafluofen, spinosad, spirodiclofen, spiromesifen, sulfluramid, sulfotep, sulprofos, SZI-121,
tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R-isomer), tetrasul, theta-cypermethrin, thiacloprid, thiamethoxam, thiapronil, thiatriphos, thiocyclam hydrogen oxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, triflumuron, trimethacarb, vamidothion, vaniliprole, verbutin, *Verticillium lecanii*, WL-108477, WL-40027, YI-5201, YI-5301, YI-5302, XMC, xylylcarb,
ZA-3274, zeta-cypermethrin, zolaprofos, ZXI-8901,
the compound 3-methyl-phenyl-propylcarbamate (Tsumacide Z), the compound 3-(5-chloro-3-pyridinyl)-8-(2,2,2-trifluoroethyl)-8-azabicyclo[3.2.1]octan-3-carboritrile (CAS-Reg.-Nr. 185982-80-3) and the corresponding 3-endo-isomer (CAS-Reg.-Nr. 185984-60-5) (cf. WO 96/37494, WO 98/25923),
as wells as preparations, which contain insecticidally active plant extracts, nematodes, fungi or viruses.

A mixture with other known active compounds, such as herbicides, or with fertilizers, growth regulators, safeners or semiochemicals is also possible.

Further, the active compounds of the formula (I) of the present invention can exist also as a mixed agent with a synergist and such formulations and application forms can be mentioned as commercially useful. Said synergist itself must not be active, but is a compound that enhances the action of the active compound.

The content of the active compounds of the formula (I) of the present invention in a commercially useful application form can be varied in a wide range.

The concentration of the active compounds of the formula (I) of the present invention at the time of application can be, for example, in the range of 0.0000001 to 100% by weight, preferably in the range of 0.00001 to 1% by weight.

The compounds of the formula (I) of the present invention can be used by usual methods suitable to the application forms.

In case of application against hygienic pests and stored grain pests the active compounds of the present invention have a good stability against alkali on a calcific substance and further show an excellent residual effectiveness in wood and soil.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. By plant cultivars are meant plants having new properties ("traits"), bred either by conventional breeding, by mutagenesis or by recombinant DNA techniques. They may be cultivars, biotypes and genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The preferred transgenic plants or plant cultivars (i.e. those obtained by gene-tic engineering) which are to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapevines), and particular emphasis is given to maize, soya beans, potatoes, cotton and oilseed rape. Traits that are emphasized are in particular increased defence of the plants against insects by toxins formed in the plants, in particular those formed by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are increased defence of plants against fungi, bacteria and viruses by systematic acquired resistance (SAR), systemine, phytoalexins, elicitors and resistance genes and corresponding expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these or still to be developed genetic traits, which plants will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or the mixtures specifically mentioned in the present text.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., Bovicola spp., *Wemeckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattella germanica* and *Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Stemostoma* spp. and *Varroa* spp.

From the order of the Actinedida (Prostigmata) und Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) according to the invention can be used as formulations (for example powders, emulsions, free-flowing compositions), which comprise the active compounds according to the invention in an amount of 1 to 80% by weight, directly or after 100 to 10000-fold dilution, or they can be used as a chemical bath.

It has furthermore been found that the compounds according to the invention have a strong insecticidal action against insects which destroy industrial materials. The following insects may be mentioned as examples and as preferred— but without a limitation:

Beetles, such as

*Hylotrupes bajulus, Chlorophorus pilosis, Anobium punctatum, Xestobium rufovillosum, Ptilinus pecticomis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus.*

Hymenopterons, such as

*Sirex juvencus, Urocerus gigas, Urocerus gigas taignus, Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccarina.*

Industrial materials in the present connection are to be understood as meaning nonliving materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agents according to the invention or mixtures comprising these are to be understood as meaning, for example:

building timber, wooden beams, railway sleepers, bridge components, boat jetties, wooden vehicles, boxes, pallets, containers, telegraph poles, wood panelling, wooden window frames and doors, plywood, chipboard, joinery or wooden products which are used quite generally in housebuilding or in building joinery.

The active compounds according to the invention can be used as such, in the form of concentrates or in generally customary formulations, such as powders, granules, solutions, suspensions, emulsions or pastes.

The formulations mentioned can be prepared in a manner known per se, for example by mixing the active compounds according to the invention with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, provided that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-coumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or a drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29268. The compounds mentioned in this document are an explicit constituent of the present application.

Especially preferred mixing partners which may be mentioned are insecticides, such as chlorpyriphos, phoxim, silafluofin, alphamethrin, cyfluthrin, cyperrnethrin, deltamethrin, permethrin, imidacloprid, NI-25, flufenoxuron, hexaflumuron, transfluthrin, thiacloprid, methoxyfenozide and triflumuron, and also fungicides, such as epoxyconazole, hexaconazole, azaconazole, piopiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The compounds according to the invention can at the same time be employed for protecting objects which come into contact with saltwater or brackish water, such as hulls, screens, nets, buildings, moorings and signalling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl (bispyridine)-bismuth chloride, tri-n-butyltin fluoride, manganese ethylene-bisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:

algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;

fungicides such as
benzo[b]thiophenecarboxylic acid cyclohexylamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole;

molluscicides such as
fentin acetate, metaldehyde, methiocarb, niclosamid, thiodicarb and trimethacarb;

or conventional antifouling active compounds such as
4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730–732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds according to the invention are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all development stages. These pests include:

From the order of the Scorpionidea, for example, *Buthus occitanus*.

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus* and *Dermatophagoides forinae*.

From the order of the Araneae, for example, *Aviculariidae* and *Araneidae*.

From the order of the Opiliones, for example, *Pseudoscorpiones chelifer, Pseudoscorpiones cheiridium* and *Opiliones phalangium*.

From the order of the Isopoda, for example, *Oniscus asellus* and *Porcellio scaber*.

From the order of the Diplopoda, for example, *Blaniulus guttulatus* and *Polydesmus* spp.

From the order of the Chilopoda, for example, *Geophilus* spp.

From the order of the Zygentoma, for example, *Ctenolepisma* spp., *Lepisma saccharina* and *Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa* and *Supella longipalpa*.

From the order of the Saltatoria, for example, *Acheta domesticus*.

From the order of the Dermaptera, for example, *Forficula auricularia*.

From the order of the Isoptera, for example, *Kalotermes* spp. and *Reticulitermes* spp.

From the order of the Psocoptera, for example, *Lepinatus* spp. and *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais* and *Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga camaria, Simulium* spp., *Stomoxys calcitrans* and *Tipula paludosa*.

From the order of the Lepidoptera, for example, *Achroia grisella, Galleria mellonella, Plodia interpunctella, Tinea cloacella, Tinea pellionella* and *Tineola bisselliella.*

From the order of the Siphonaptera, for example, *Ctenocephalides canis, Ctenocephalides felis, Pulex irritans, Tunga penetrans* and *Xenopsylla cheopis.*

From the order of the Hymenoptera, for example, *Camponotus herculeanus, Lasius faliginosus, Lasius niger, Lasius umbratus, Monomorium pharaonis, Paravespula* spp. and *Tetramorium caespitum.*

From the order of the Anoplura, for example, *Pediculus humanus capitis, Pediculus humanus corporis* and *Phthirus pubis.*

From the order of the Heteroptera, for example, *Cimex hemipterus, Cimex lectularius, Rhodinus prolixus* and *Triatoma infestans.*

In the field of household insecticides, they are used alone or in combination with other suitable active compounds, such as phosphoric acid esters, carbamates, pyrethroids, growth regulators or active compounds from other known classes of insecticides.

They are used as aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive evaporation systems, moth papers, moth bags and moth gels, as granules or dusts, in baits for spreading or in bait stations.

Then the present invention will be described more specifically by examples. The present invention, however, should not be restricted only to them in any way.

SYNTHESIS EXAMPLES

Synthesis Example 1

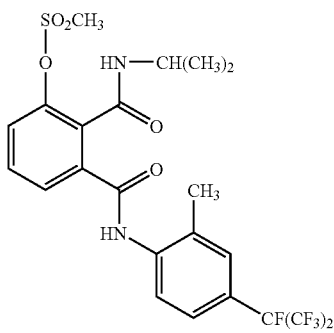

To N-(4-heptafluoroisopropyl-2-methylphenyl)-3-methanesulfonyloxyphthalimide (0.71 g), isopropylamine (1.68 g) was added and stirred at room temperature for 4 hours. After finishing the reaction, the excess of isopropylamine was distilled off under reduced pressure and the obtained residue was purified by silica gel column chromatography (gradient elution n-hexane/ethyl acetate=2/1 to 1/1) to obtain $N^1$(4-heptafluoroisopropyl-2-methylphenyl)-N-2-isopropyl-3-methanesulfonyloxyphthalamide (0.43 g) having the melting point of 168–170° C.

Synthesis Example 2

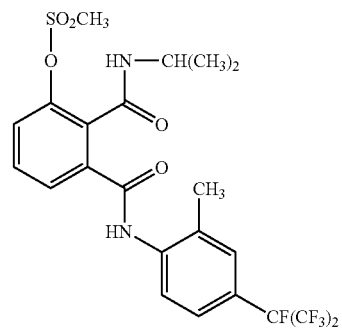

An acetonitrile solution (20 mL) of N-isopropyl-6-N-isopropyl-6-methanesulfonyloxyphthalisoimide crude product (1.68 g) and 4-heptafluoroisopropyl-2-methylaniline (1.65 g) was stirred at 50° C. for 5 hours. After finishing the reaction, the solvent was distilled off under reduced pressure and the obtained residue was purified by silica gel column chromatography (gradient elution n-hexane/ethyl acetate=2/1 to 1/1) to obtain the same compound as in Synthesis Example 1 (0.89 g).

Synthesis Example 3

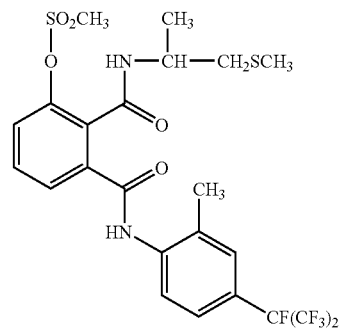

After adding methanesulfonyl chloride (0.69 g) to a 1,2-dichloroethane solution (14 mL) of 3-hydroxyphthalic anhydride (0.82 g) and triethylamine (0.76 g) at room temperature, the mixture was stirred at 50° C. for 1.5 hours. After bringing the reaction solution to room temperature, 1-methyl-2-(methylthio)ethylamine (0.74 g) and triethylamine (0.76 g) were added under ice cooling and the mixture was further stirred at room temperature for 2 hours. After washing the reaction solution with 1N aqueous solution of hydrochloric acid (20 mL), aqueous solution (10 mL) of sodium hydrogen carbonate (0.84 g) and methyl chlorocarbonate (0.62 g) were added to the separated organic layer and the mixture was stirred at 50° C. for 2 hours. The organic layer was separated, to which 4-heptafluoroisopropyl-2-methylaniline (1.24 g) and concentrated hydrochloric acid (6 drops) were added, and stirred at 50° C. for 1 hour.

After the reaction solution was naturally cooled to room temperature, the solvent was distilled off under reduced pressure and the obtained residue was purified by silica gel column chromatography (gradient elution n-hexane/ethyl acetate=2/1 to 1/1) to obtain $N^1$-(4-heptafluoroisopropyl-2-methylphenyl)-$N^2$-[1-methyl-2-(methylthio)-ethyl]-3-methanesulfonyloxyphthalamide (1.30 g) having the melting point of 101–103° C.

Synthesis Example 4

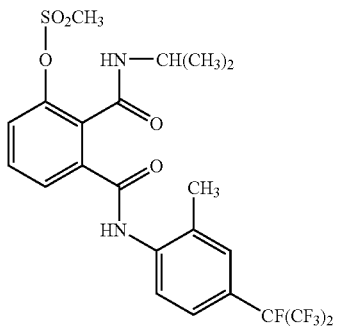

To an acetonitrile solution (10 mL) of N-(4-heptafluoroisopropyl-2-methylphenyl)-6-methanesulfonyloxyphthalisoimide (0.45 g), isopropylamine (0.06 g) was added and the mixture was stirred at room temperature for 2 days. After finishing the reaction, the solvent was distilled off under reduced pressure and the obtained residue was purified by silica gel column chromatography (gradient elution n-hexane/ethyl acetate=2/1 to 1/1) to obtain the same compound as in Synthesis Example 1 (0.13 g).

Synthesis Example 5

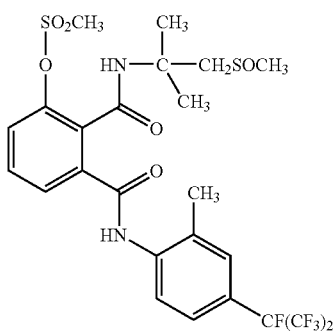

To a 1,2-dichloroethane (10 mL) solution of $N^2$-[1,1-dimethyl-2-(methylthio)ethyl]-$N^1$-(4-heptafluoroisopropyl-2-methylphenyl)-3-methanesulfonyloxyphthalamide (0.6 g), hydrogen peroxide (0.54 g), formic acid (0.03 g) and water (1 mL) were added and the mixture was stirred at 50° C. for 4 hours. After naturally cooling it to room temperature, the organic layer was consecutively washed with aqueous solution of sodium thiosulfate and saturated aqueous solution of sodium chloride and dried with anhydrous sodium sulfate. After distilling off the solvent, the obtained residue was purified by silica gel column chromatography (gradient elution n-hexane/ethyl acetate=3/1 to 1/1) to obtain $N^2$-[1,1-dimethyl-2-(methylsulfinyl)ethyl]-$N^1$-(4-heptafluoroisopropyl-2-methylphenyl)-3-methanesulfonyloxyphthalamide (0.59 g) having the melting point of 85–88° C.

Synthesis Example 6

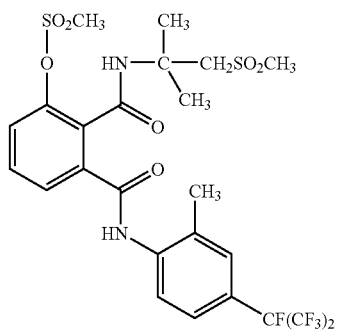

To a dichloroethane solution (10 mL) of $N^2$-[1,1-dimethyl-2-(methylthio)ethyl]-$N^1$-(4-heptafluoroisopropyl-2-methylphenyl)-3-methanesulfonyloxyphthalamide (0.51 g), m-chloroperbenzoic acid (0.36 g) was added and the mixture was stirred at room temperature for 5 hours. After finishing the reaction, the reaction solution was consecutively washed with aqueous solution of sodium thiosulfate, saturated aqueous solution of sodium bicarbonate and saturated aqueous solution of sodium chloride and dried with anhydrous sodium sulfate. After distilling off the solvent, the obtained residue was purified by silica gel column chromatography (gradient elution n-hexane/ethyl acetate=2/1 to 1/1) to obtain $N^2$-[1,1-dimethyl-2-(methylsulfonyl)ethyl]-$N^1$-(4-heptafluoroisopropyl-2-methylphenyl)-3-methanesulfonyloxyphthalamide (0.41 g) having the melting point of 93–97° C.

The compounds obtained in the same manner to the above-mentioned Synthesis Examples 1 to 6 are shown in the following Table 1, together with the compounds synthesized in Synthesis Examples 1 to 6.

TABLE 1

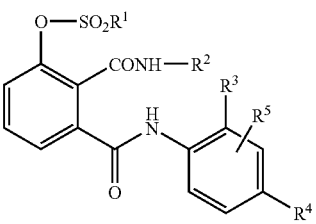

| No. | $R^1$ | $R^2$ | $R^3$ | $R^4$ | $R^5$ | MP/° C. |
|---|---|---|---|---|---|---|
| 1 | $CH_3$ | $CH(CH_3)_2$ | $CH_3$ | $CF(CF_3)_2$ | H | 168–170 |
| 2 | $CH_3$ | $CH(CH_3)CH_2CH_3$ | $CH_3$ | $CF(CF_3)_2$ | H | 187–189 |

TABLE 1-continued

![structure]

| No. | R¹ | R² | R³ | R⁴ | R⁵ | MP/° C. |
|---|---|---|---|---|---|---|
| 3 | $CH_3$ | $C(CH_3)_3$ | $CH_3$ | $CF(CF_3)_2$ | H | 119–121 |
| 4 | $CH_3$ | cyclopropyl | $CH_3$ | $CF(CF_3)_2$ | H | * |
| 5 | $CH_3$ | $CH(CH_3)CH_2SCH_3$ | H | $CF(CF_3)_2$ | H | 181–182 |
| 6 | $CH_3$ | $CH(CH_3)CH_2SCH_3$ | $CH_3$ | $OCF_3$ | H | 129–132 |
| 7 | $CH_3$ | $CH(CH_3)CH_2SCH_3$ | $CH_3$ | $CF(CF_3)_2$ | H | 101–103 |
| 8 | $CH_3$ | $CH(CH_3)CH_2SOCH_3$ | $CH_3$ | $CF(CF_3)_2$ | H | 221–223 |
| 9 | $CH_3$ | $CH(CH_3)CH_2SO_2CH_3$ | $CH_3$ | $CF(CF_3)_2$ | H | 102–107 |
| 10 | $CH_3$ | $C(CH_3)_2CH_2SCH_3$ | $CH_3$ | $CF(CF_3)_2$ | H | 97–99 |
| 11 | $CH_3$ | $C(CH_3)_2CH_2SOCH_3$ | $CH_3$ | $CF(CF_3)_2$ | H | 85–88 |
| 12 | $CH_3$ | $C(CH_3)_2CH_2SO_2CH_3$ | $CH_3$ | $CF(CF_3)_2$ | H | 93–97 |
| 13 | $CH_2CH_3$ | $CH(CH_3)_2$ | $CH_3$ | $CF(CF_3)_2$ | H | ** |
| 14 | $CH_2CH_3$ | $CH(CH_3)CH_2SCH_3$ | $CH_3$ | $CF(CF_3)_2$ | H | 112–114 |
| 15 | $CH_2CH_3$ | $CH(CH_3)CH_2SOCH_3$ | $CH_3$ | $CF(CF_3)_2$ | H | |
| 16 | $CH_2CH_3$ | $CH(CH_3)CH_2SO_2CH_3$ | $CH_3$ | $CF(CF_3)_2$ | H | 194–196 |
| 17 | $CH_2CH_3$ | $C(CH_3)_2CH_2SCH_3$ | $CH_3$ | $CF(CF_3)_2$ | H | 86–91 |
| 18 | $CH_2CH_3$ | $C(CH_3)_2CH_2SOCH_3$ | $CH_3$ | $CF(CF_3)_2$ | H | *** |
| 19 | $CH_2CH_3$ | $C(CH_3)_2CH_2SO_2CH_3$ | $CH_3$ | $CF(CF_3)_2$ | H | 85–89 |
| 20 | $CF_3$ | $CH(CH_3)_2$ | $CH_3$ | $CF(CF_3)_2$ | H | |
| 21 | $CF_3$ | $CH(CH_3)CH_2SCH_3$ | $CH_3$ | $CF(CF_3)_2$ | H | 209–214 |
| 22 | $CF_3$ | $CH(CH_3)CH_2SOCH_3$ | $CH_3$ | $CF(CF_3)_2$ | H | |
| 23 | $CF_3$ | $CH(CH_3)CH_2SO_2CH_3$ | $CH_3$ | $CF(CF_3)_2$ | H | 136–138 |
| 24 | $CH_3$ | $C(CH_3)_2CH_2SCH_3$ | Cl | Cl | 3-Cl | 193–195 |
| 25 | $CH_3$ | $C(CH_3)_2CH_2SOCH_3$ | Cl | Cl | 3-Cl | 135–140 |
| 26 | $CH_3$ | $C(CH_3)_2CH_2SO_2CH_3$ | Cl | Cl | 3-Cl | 200–203 |

* ¹H-NMR (CDCl₃, ppm): 0.5–0.8 (4H, m), 2.3 (3H, s), 2.8 (1H, m), 3.2 (3H, s), 6.5 (1H, bs), 6.7 (1H, d), 7.3–7.7 (4H, m), 8.1 (1H, d), 8.4 (1H, bs).
** ¹H-NMR (CDCl₃, ppm): 1.6 (9H, m), 2.1 (3H, s), 2.4 (3H, s), 3.0 (2H, m), 3.5 (3H, q), 6.9 (1H, bs), 7.4–7.6 (4H, m), 8.2 (1H, d), 8.4 (1H, bs).
*** ¹H-NMR (CDCl₃, ppm): 1.2 (6H, d), 1.5 (3H, t), 2.4 (3H, s), 3.4 (2H, q), 4.2 (1H, m), 6.2 (1H, bd), 7.4–7.7 (5H, m), 8.2 (1H, bd), 8.5 (1H, bs).

Referential Example 1

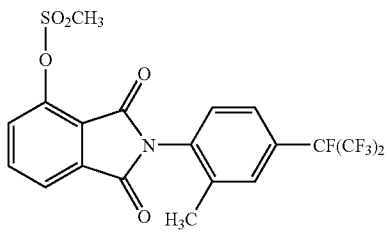

To a tetrahydrofuran solution (50 mL) of N-(4-heptafluoroisopropyl-2-methylphenyl)-3-hydroxyphthalimide (3.60 g) and triethylamine (1.73 g), methanesulfonyl chloride (1.18 g) was added drop by drop under ice cooling and the mixture was stirred at room temperature for 8 hours. After finishing the reaction, the solvent was distilled off under reduced pressure and the obtained residue was dissolved in ethyl acetate (50 mL), washed consecutively with 2N hydrochloric acid and saturated aqueous solution of sodium chloride and dried with anhydrous sodium sulfate. After distilling off the solvent under reduced pressure, the crude product was washed with a mixed solvent of ether and n-hexane to obtain N-(4-heptafluoroisopropyl-2-methylphenyl)-3-methanesulfonyloxyphthalimide (4.04 g) having the melting point of 154–155° C.

Referential Example 2

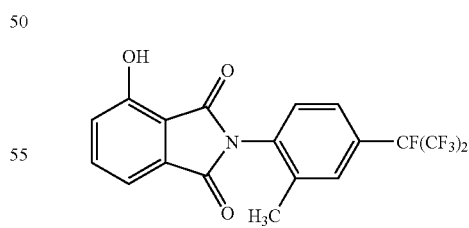

3-Hydroxyphthalic anhydride (7.29 g) and 4-heptafluoroisopropyl-2-methylaniline (12.22 g) in acetic acid (100 mL) were refluxed for 6 hours. After finishing the reaction, the solvent was distilled off under reduced pressure and the obtained residue was washed with a mixed solvent of ether and n-hexane to obtain N-(4-heptafluoroisopropyl-2-methylphenyl)-3-hydroxyphthalimide (11.23 g) having the melting point of 180–182° C.

Referential Example 3

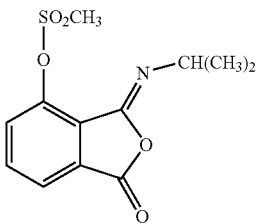

To a toluene solution (20 mL) of N-isopropyl-3-methane-sulfonyl-oxyphthalamic acid (1.80 g), trifluoroacetic anhydride (3.76 g) was added and the mixture was stirred at room temperature for 1 hour. After finishing the reaction, the solvent and the excess of trifluoroacetic anhydride were distilled off under reduced pressure to obtain N-isopropyl-6-methanesulfonyloxyphthalisoimide (1.68 g). The obtained object was used for the next reaction without purification.

Referential Example 4

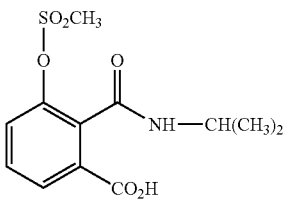

Isopropylamine (0.78 g) was added to an acetonitrile solution (10 mL) of 3-methanesulfonyloxyphthalic anhydride (1.60 g) under ice cooling and the mixture was further stirred at room temperature for 8 hours. After finishing the reaction, the solvent and the excess of isopropylamine were distilled off under reduced pressure and the obtained crude product was washed with a small amount of acetonitrile to obtain N-isopropyl-3-methanesulfonyloxyphthalamic acid (1.80 g) having the melting point of 56–59° C.

Referential Example 5

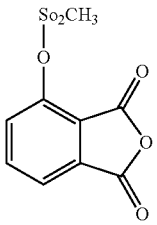

Triethylamine (0.83 g) and methanesulfonyl chloride (0.89 g) were added to a THF solution (10 mL) of 3-hydroxyphthalic anhydride (1.22 g) under ice cooling and the mixture was stirred at room temperature for 8 hours. After finishing the reaction, ether (20 mL) was added and the mixture was washed consecutively with water and saturated aqueous solution of sodium chloride and dried with anhydrous sodium sulfate. After distilling off the solvent under reduced pressure, the crude product was washed with a mixed solvent of ether and n-hexane to obtain 3-methanesulfonyloxyphthalic anhydride (1.75 g) having the melting point of 134–140° C.

Referential Example 6

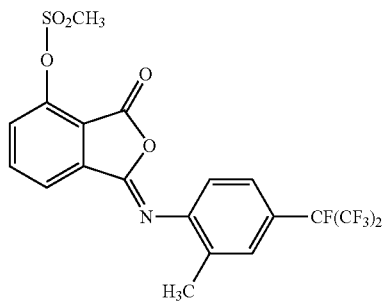

To a 1,2-dichloroethane solution (30 mL) of N-(4-heptafluoroisopropyl-2-methylphenyl)-6-methanesulfonyloxyphthalamic acid (1.01 g), an aqueous solution (5mL) of sodium hydrogen carbonate (0.27 g) and methyl chlorocarbonate (0.24 g) were consecutively added and the mixture was stirred at 50° C. for 3 hours. After finishing the reaction, the organic layer was separated and dried with anhydrous sodium sulfate. Then the solvent was distilled off under reduced pressure to obtain N-(4-heptafluoro is opropyl-2-methylphenyl)-6-methanesulfonyloxyphthalisoimide (0.49 g) having the refractive index $n_D^{20}$ 1.4430.

Referential Example 7

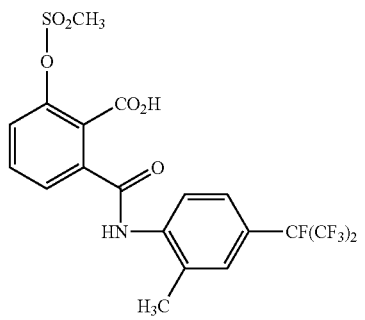

To an acetonitrile solution (10 mL) of 3-methanesulfonyloxyphthalic anhydride (0.51 g), 4-heptafluoroisopropyl-2-methylaniline (0.58 g) was added drop by drop under ice cooling and the mixture was stirred at room temperature for 4 hours. After finishing the reaction, the solvent was distilled off under reduced pressure and the obtained crude product was washed with a small amount of acetonitrile to obtain N-(4-heptafluoroisopropyl-2-methylphenyl)-6-methanesulfonyloxyphthalamic acid (1.01 g) having the melting point of 64–68° C.

USE EXAMPLES

Biological Test Example 1

Test against larva of *Spodoptera litura*

Preparation of test agent:

| | | |
|---|---|---|
| Solvent: | Dimethylformamide | 3 parts by weight |
| Emulsifier: | Polyoxyethylene alkyl phenyl ether | 1 part by weight |

In order to make an appropriate formulation of an active compound 1 part by weight of the active compound was mixed with the above-mentioned amount of solvent containing the above-mentioned amount of emulsifier and the mixture was diluted with water to a prescribed concentration.

Test Method:

Leaves of sweet potato were soaked in the test agent diluted to a prescribed concentration with water, dried in the air and put in a dish of 9 cm diameter. 10 larvae of *Spodoptera litura* at the third instar were placed on the leaves and kept in a room at constant temperature of 25° C. After 2 and 4 days further leaves of sweet potato were added and after 7 days the number of dead larvae was counted and the rate of death was calculated.

In this test the results of 2 dishes at 1 section were averaged.

Test Results

As specific examples the compounds of the compound no. 1, 2, 3, 4, 5, 6, 7, 8, 9, 10, 11, 12, 13, 14, 16, 17, 18, 19, 21, 23, 24, 25 and 26 showed 100% of rate of death at 20 ppm concentration of effective component.

Biological Test Example 2

Test Against Larva of *Cnaphalocrocis medinalis* Guenee

Test Method:

Root parts of paddy rice (variety: Tamanishiki) cultivated to 4 to 5 leaf stage were put in a brown bottle filled with the diluted aqueous solution of the prescribed concentration of the active compound prepared in the same manner as in the above-mentioned Biological Test Example 1. Three days after the treatment with the agent, ⅓ amount of rice plant was collected and their foliage part was cut in 4 to 5 cm length, which were put in a dish with 9 cm diameter with a sheet of filter paper wetted with 2 mL of water. Five larvae of *Cnaphalocrocis medinalis* Guenee at the second instar were put in the dish which was placed in a room at constant temperature of 25° C. After 2 and 4 days, each rest (each ⅓ amount) of foliage parts of rice plant were cut in the same manner and added to the dish. After 7 days the number of dead larvae was counted and the rate of death was calculated. In this test the results of 2 dishes at 1 section were averaged.

Test Results

As specific examples the compounds of the compound no. 1, 5, 7, 8, 9, 10, 11 and 12 showed 100% of rate of death at 20 ppm concentration of effective component.

Formulation Example 1 (Granule)

To a mixture of 10 parts of the compound of the present invention (No. 1), 30 parts of bentonite (montmorillonite), 58 parts of talc and 2 parts of ligninsulfonate salt, 25 parts of water are added, well kneaded, made into granules of 10 to 40 mesh by an extrusion granulator and dried at 40 to 50° C. to obtain granules.

Formulation Example 2 (Granules)

Ninety-five (95) parts of clay mineral particles having particle diameter distribution in the range of 0.2 to 2 mm are put in a rotary mixer. While rotating it, 5 parts of the compound of the present invention (No. 5) are sprayed together with a liquid diluent, wetted uniformly and dried at 40 to 50° C. to obtain granules.

Formulation Example 3 (Emulsifiable Concentrate)

Thirty (30) parts of the compound of the present invention (No. 11), 55 parts of xylene, 8 parts of polyoxyethylene alkyl phenyl ether and 7 parts of calcium alkylbenzenesulfonate are mixed and stirred to obtain an emulsifiable concentrate.

Formulation Example 4 (Wettable Powder)

Fifteen (15) parts of the compound of the present invention (No. 17), 80 parts of a mixture of white carbon (hydrous amorphous silicon oxide fine powders) and powder clay (1:5), 2 parts of sodium alkylbenzenesulfonate and 3 parts of sodium alkylnaphthalenesulfonate-formalin-condensate are crushed and mixed to make a wettable powder.

Formulation Example 5 (Water Dispersible Granule)

Twenty (20) parts of the compound of the present invention (No. 8), 30 parts of sodium ligninsulfonate, 15 parts of bentonite and 35 parts of calcined diatomaceous earth are well mixed, added with water, extruded with 0.3 mm screen and dried to obtain water dispersible granules.

What is claimed is:

1. A phthalamide derivative of formula (I)

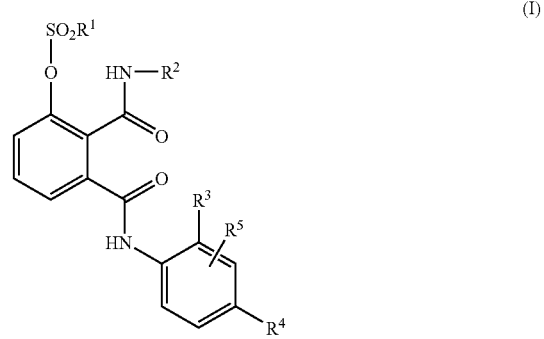

(I)

wherein
$R^1$ represents alkyl that is optionally halogen-substituted,
$R^2$ represents alkyl that is optionally substituted or cycloalkyl that is optionally substituted,
$R^3$ represents hydrogen, halogen, or alkyl that is optionally halogen-substituted, R⁴ represents hydrogen, halogen-substituted alkyl, halogen-substituted alkoxy, halogen-substituted phenyl, or halogen-substituted phenoxy, and R⁵ represents hydrogen, halogen, or alkyl that is optionally halogen-substituted.

2. A compound according to claim 1 wherein

R¹ represents $C_{1-6}$ alkyl that is optionally fluoro-substituted, chloro-substituted, or bromo-substituted, R² represents $C_{1-6}$ alkyl that is optionally fluoro-substituted, chloro-substituted, bromo-substituted, $C_{1-4}$ alkoxy-substituted, $C_{1-4}$ alkylthio-substituted, $C_{1-4}$ alkylsulfinyl-substituted, or $C_{1-4}$ alkylsulfonyl-substituted; or represents $C_{3-6}$ cycloalkyl that is optionally halogen-substituted or $C_{1-4}$ alkyl-substituted, R³ represents hydrogen or halogen; or represents $C_{1-6}$ alkyl that is optionally fluoro-substituted, chloro-substituted, or bromo-substituted, R⁴ represents hydrogen, halogen-substituted $C_{1-6}$ alkyl, halogen-substituted $C_{1-6}$ alkoxy, halogen-substituted phenyl, or halogen-substituted phenoxy, and R⁵ represents hydrogen or halogen; or represents $C_{1-6}$ alkyl that is optionally fluoro-substituted, chloro-substituted, or bromo-substituted.

3. A compound according to claim 1 wherein

R¹ represents methyl, ethyl, propyl, or trifluoromethyl,

R² represents methyl, ethyl, n-propyl, isopropyl, n-butyl, isobutyl, sec-butyl, tert-butyl, n-pentyl, isopentyl, sec-pentyl, tert-pentyl, n-hexyl, isohexyl, sec-hexyl, methylthiomethyl, ethylthiomethyl, methylthioethyl, ethylthioethyl, methylthiopropyl, ethylthiopropyl, methylthiobutyl, ethylthiobutyl, methylthiopentyl, ethylthiopentyl, methylsulfinylmethyl, ethylsulfinylmethyl, methylsulfinylethyl, ethylsulfinylethyl, methylsulfinylpropyl, ethylsulfinylpropyl, methylsulfinylbutyl, ethylsulfinylbutyl, methylsulfinylpentyl, ethylsulfinylpentyl, methylsulfonylmethyl, ethylsulfonylmethyl, methylsulfonylethyl, ethylsulfonylethyl, methylsulfonylpropyl, ethylsulfonylpropyl, methylsulfonylbutyl, ethylsulfonylbutyl, methylsulfonylpentyl, or ethylsulfonylpentyl; or represents cyclopropyl, cyclobutyl, cyclopentyl, or cyclohexyl, each of which is optionally substituted with fluoro, chloro, bromo, methyl, or ethyl, R³ represents hydrogen, fluoro, chloro, bromo, methyl, ethyl, or trifluoromethyl, R⁴ represents fluoro, chloro, or bromo; or represents methyl, ethyl, n-propyl, isopropyl, n-butyl, isobutyl, sec-butyl, tert-butyl, methoxy, ethoxy, n-propoxy, or isopropoxy, each of which is optionally substituted with one or more fluoro, perfluoro-substituted, or substituted with one or more fluoro and 1 or 2 chloro, and R⁵ represents hydrogen, fluoro, chloro, or bromo; or represents methyl or ethyl, each of which is optionally fluoro-substituted or chloro-substituted.

4. A compound according to claim 1 wherein

R¹ represents methyl or ethyl,

R2 represents isopropyl, tert-butyl, 1-methyl-2-(methylthio)ethyl, 1,1-dimethyl-2-(methylthio)ethyl, 1-methyl-2-(methylsulfinyl)ethyl, 1,1-d imethyl-2-(methylsulfinyl)ethyl, 1-methyl-2-(methylsulfonyl)ethyl, or 1,1-d imethyl-2-(methylsulfonyl)ethyl, R³ represents methyl, R⁴ represents perfluoroisopropyl, and R⁵ represents hydrogen.

5. A process for the preparation of a compounds of formula (I) according to claim 1 comprising (a) reacting a compound of formula (II)

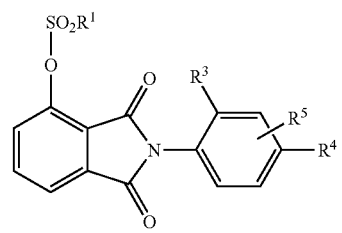

(II)

wherein R¹, R³, R⁴, and R⁵ have the same definitions as for formula (I) of claim 1, with a compound of formula (III)

$H_2N—R^2$ (III)

wherein R² has the same definition as for formula (I) in claim 1, in the presence of inert solvents and optionally in the presence of a base, or (b) reacting a compound of formula (IV)

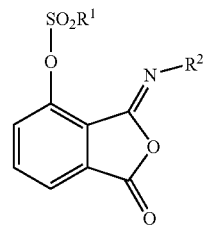

(IV)

wherein R¹ and R² have the same definitions as for formula (I) in claim 1, with a compound of formula (V)

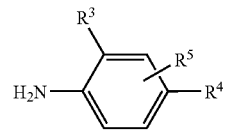

(V)

wherein R³, R⁴, and R⁵ have the same definitions as for formula (I) in claim 1, in the presence of inert solvents and optionally in the presence of an acid catalyst, or (c) reacting a compound of formula (VI)

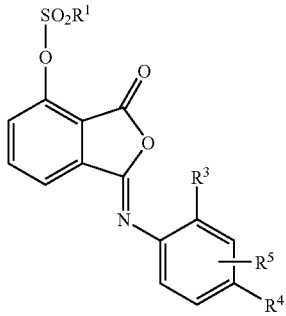

wherein $R^1$, $R^3$, $R^4$, and $R^5$ have the same definitions as for formula (I) in claim 1, with a compound of formula (III), $$H_2N-R^2 \quad (III)$$

wherein $R^2$ has the same definition as for formula (I) in claim 1, in the presence of inert solvents and optionally in the presence of a acid catalyst, or (d) for compounds of formula (I) in which $R^2$ represents alkylsulfinylalkyl or alkylsulfonylalkyl, reacting a compound of formula (Id)

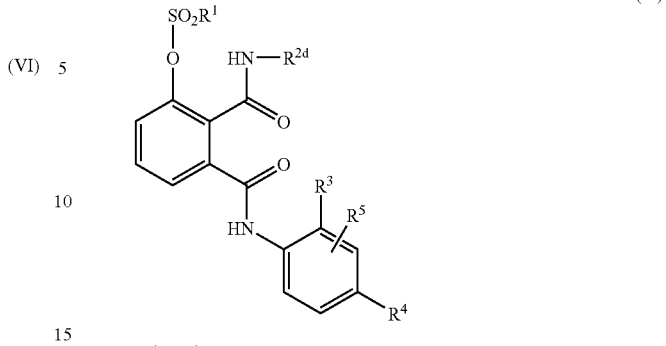

wherein $R^{2d}$ represents alkyithioalkyl, and $R^1$, $R^3$, $R^4$, and $R^5$ have the same definitions as for formula (I) in claim 1, with an oxidizing agent in the presence of inert solvents.

6. An insecticidal composition containing one or more phthalamide derivatives of formula (I) according to claim 1.

7. A process for combating insects comprising allowing an effective amount of one or more phthalamide derivatives of formula (I) according to claim 1 to act on the insects and/or their habitat.

8. A process for the preparation of insecticidal compositions comprising mixing one or more phthalamide derivatives of formula (I) according to claim 1 with one or more extenders and/or surface active agents.

* * * * *